United States Patent
Machida et al.

(10) Patent No.: US 12,304,932 B2
(45) Date of Patent: May 20, 2025

(54) PACAP STABILIZED PEPTIDE

(71) Applicant: SENJU PHARMACEUTICAL CO., LTD., Osaka (JP)

(72) Inventors: Shinnosuke Machida, Osaka (JP); Takeshi Nakajima, Osaka (JP)

(73) Assignee: SENJU PHARMACEUTICAL CO., LTD., Osaka (JP)

( * ) Notice: Subject to any disclaimer, the term of this patent is extended or adjusted under 35 U.S.C. 154(b) by 950 days.

(21) Appl. No.: 16/763,732

(22) PCT Filed: Nov. 14, 2018

(86) PCT No.: PCT/JP2018/042196
§ 371 (c)(1),
(2) Date: May 13, 2020

(87) PCT Pub. No.: WO2019/098254
PCT Pub. Date: May 23, 2019

(65) Prior Publication Data
US 2020/0347107 A1    Nov. 5, 2020

(30) Foreign Application Priority Data
Nov. 14, 2017  (JP) .................. 2017-219181

(51) Int. Cl.
*C07K 14/47* (2006.01)
*A61K 38/00* (2006.01)

(52) U.S. Cl.
CPC .......... *C07K 14/4705* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,538,995 A * | 7/1996 | Matsumura | ........ | C07D 307/937 549/465 |
| 5,623,050 A * | 4/1997 | Kitada | ........ | C07K 1/006 530/324 |
| 5,747,531 A | 5/1998 | Matsumura et al. | | |
| 2009/0111730 A1 | 4/2009 | Dorwald et al. | | |
| 2011/0212899 A1 | 9/2011 | Takayama et al. | | |
| 2011/0268789 A1 | 11/2011 | Li et al. | | |
| 2013/0065816 A1 * | 3/2013 | Coy | ........ | A61K 33/243 514/6.9 |

FOREIGN PATENT DOCUMENTS

| | | | |
|---|---|---|---|
| CN | 102215859 | 10/2011 | |
| CN | 103145851 | 6/2013 | |
| JP | 7-228581 | 8/1995 | |
| JP | 9-110729 | 4/1997 | |
| JP | 10-505863 | 6/1998 | |
| JP | 2004-256547 | 9/2004 | |
| JP | 2009269818 | * 11/2009 | |
| JP | 2012-232952 | 11/2012 | |
| JP | 2013-509450 | 3/2013 | |
| JP | 2014-510101 | 4/2014 | |
| JP | 2001-226284 | 8/2021 | |
| WO | 96/09318 | 3/1996 | |
| WO | WO-9609318 A1 | * 3/1996 | ....... C07K 14/57563 |
| WO | 2005/102375 | 11/2005 | |
| WO | 2006/005667 | 1/2006 | |
| WO | 2011/054001 | 5/2011 | |
| WO | 2012/127475 | 9/2012 | |

OTHER PUBLICATIONS

Zhao et al., Chemistry. Feb. 24, 2016; 22(9): 3009-3018 (Year: 2016).*
Sureshbabu et al., Tetrahedron Letters, vol. 48, pp. 7038-7041, 2007 (Year: 2007).*
Jason Herr, Biorg & Med. Chem., 2002, vol. 10, pp. 3379-3393 (Year: 2002).*
R. Jason Herr, Bioorganic and Medicinal Chemistry, 2002, vol. 10, pp. 3379-3393 (Year: 2002).*
Sureshbabu et al., "Synthesis of tetrazole analogues of amino acids using Fmoc chemistry: isolation of amino free tetrazoles and their incorporation into peptides", Tetrahedron Letters, 2007, vol. 48, pp. 7038-7041, 4 pages.
Bourgault, S. et al., "Pituitary Adenylate Cyclase-Activating Polypeptide: Focus on Structure-Activity Relationships of a Neuroprotective Peptide", Current Medicinal Chemistry, 2009, vol. 16, pp. 4462-4480.
International Search Report issued Jan. 29, 2019 in corresponding International (PCT) Application No. PCT/JP2018/042196.
Dickson, L. et al., "VPAC and PAC receptors: From ligands to function", Pharmacology & Therapeutics, 2009, vol. 121, pp. 294-316.

\* cited by examiner

*Primary Examiner* — Melissa L Fisher
*Assistant Examiner* — Joseph Fischer
(74) *Attorney, Agent, or Firm* — Wenderoth, Lind & Ponack, L.L.P.

(57) ABSTRACT

The purpose of the present invention is to provide a PACAP peptide having increased stability. The problem is solved by the discovery that substituting a carboxy group of the position 3 and/or position 8 aspartic acid in the PACAP sequence by tetrazole significantly enhances stability.

6 Claims, 2 Drawing Sheets
Specification includes a Sequence Listing.

(PAC1R)

(VPAC1R)

Peptide1

Peptide2

Peptide6

Peptide7

Peptide8

Peptide9

PACAP STABILIZED PEPTIDE

FIELD

The present invention relates to a stabilized peptide having PACAP physiological activity, and to a neuroprotective agent, a corneal neurite formation promoting agent, a lacrimal secretion promoting agent, a dry-eye treatment agent, a corneal epithelial damage treatment agent, a corneal endothelial damage treatment agent, a vascular endothelial function ameliorating agent, an anti-inflammatory agent or a pharmaceutical composition, which comprises the peptide.

BACKGROUND

Nerve cells are cells composing the nervous system, which is largely divided into the central nervous system and the peripheral nervous system. Nerve cells are susceptible to damage by external factors, including cerebrovascular disease such as stroke and cerebral infarction, and internal factors including accumulation of abnormal proteins, oxidative stress and inflammation, while nerve cells also have low regenerative capacity, and therefore when nerve cells are damaged, nerve cells damage causes a remarkable reduction of patient QOL. Neurodegenerative diseases associated with neurodegeneration and neurologic deficit in the central nervous system include neurodegenerative diseases such as Alzheimer's disease, Parkinson's disease, Huntington's disease, amyotrophic lateral sclerosis and multiple sclerosis, as well as sensory neurodegenerative diseases including optic neurodegenerative diseases such as glaucoma, and also nerve deafness.

Advances in neuroscience have led to the discovery of numerous neuroprotective factors, which has brought hope of developing preventions and treatments for nervous disorders. It has been discovered that drugs that reduce free radicals and excitatory amino acids, which are causes of neurodegeneration, or that are able to protect and/or repair nerve cells (for example, neurotrophic factors or immunophilin ligands such as immunosuppressive agents) have neuroprotective action, and in vivo proteins such as pituitary adenylate cyclase-activating polypeptide (PACAP), CD44 and human brain carboxypeptidase B (HBCPB) have been found to have neuroprotective action (PTLs 1 and 2).

Pituitary adenylate cyclase-activating polypeptide (PACAP) is a neuropeptide discovered in sheep hypothalamus extract. PACAP can exhibit activity which stimulates cAMP formation in anterior pituitary cells. PACAP includes PACAP38 consisting of 38 amino acid residues and PACAP27 consisting of 27 amino acid residues, both of which have equivalent activity (NPLs 1 and 2). PACAP belongs to the vasoactive intestinal polypeptide (VIP)/secretin/glucagon superfamily, and the sequence of human PACAP27 has 68% identity with vasoactive intestinal polypeptide (VIP). PACAP and VIP both bind to PAC1 receptor (PAC1R), VPAC1 receptor (VPAC1R) and VPAC2 receptor (VPAC2R), but they differ in their affinities. PAC1R binds to PACAP with high selectivity, with an affinity for PACAP that is more than 1000 times greater than its affinity for VIP, VPAC1R and VPAC2R, on the other hand, both have equal affinity for PACAP and VIP. PACAP has a variety of physiological effects, being known to be physiologically active as a neuroprotective substance, immunosuppressive factor, vasodilating factor, exocrine secretion promoting agent (PTL 3) and neurite formation promoting factor (PTL 4).

Pharmaceutical drug has been developed by means of the various physiological activities of PACAP. However, most peptides of relatively short length such as PACAP are usually unstable in aqueous solution and are associated with the problem of a short half-life in the body due to a lack of protease resistance.

CITATION LIST

Patent Literature

[PTL 1] JP 2014-510101
[PTL 2] JP 2012-232952
[PTL 3] JP 2009-269818
[PTL 4] WO2005/102375

Non-Patent Literature

[NPL 1] S. Bourgault (2009) Current Medicinal Chemistry 16, 4462-4480
[NPL 2] Louise Dickson (2009) Pharmacology & Therapeutics, 12, 294-316

SUMMARY

Technical Problem

It is an object of the present invention to provide a stabilized PACAP peptide, with high stability in aqueous solution, as well as a neuroprotective agent, a neurite formation promoting agent, a lacrimal gland secretion promoting agent, a therapeutic or prophylactic pharmaceutical composition for dry-eye, a therapeutic or prophylactic pharmaceutical composition for corneal epithelial damage, a therapeutic or prophylactic pharmaceutical composition for nerve disorder, a therapeutic or prophylactic pharmaceutical composition for corneal endothelial damage, or a vascular endothelial function ameliorating agent, which comprises the peptide.

Solution to Problem

As a result of extensive research for increasing the stability of PACAP in aqueous solution, the present inventors have found that the stability of PACAP peptide in aqueous solution can be drastically increased by replacing the carboxy group of aspartic acid present in PACAP peptide with tetrazole, and have arrived at the present invention.

Thus, the present invention relates to the following:

[1] A peptide consisting of a sequence or modified sequence wherein, in the sequence represented by the following formula:

(SEQ ID NO: 3)
H-$X_1$-D-G-I-F-T-D-$X_2$-Y-$X_3$-R-Y-R-$X_4$-$X_5$-$X_6$-A-$X_7$-$X_8$-$X_9$-Y-L-A-A-V-$X_{10}$

{where $X_1$ is a neutral amino acid, $X_2$ is a neutral amino acid, $X_3$ is a neutral amino acid, $X_4$ is a basic amino acid, $X_5$ is a neutral amino acid or egTz, $X_6$ is a non-polar amino acid, $X_7$ is a non-polar amino acid, $X_8$ is a basic amino acid, $X_9$ is a basic amino acid and $X_{10}$ is a non-polar amino acid}, the carboxy group of the aspartic acid residue at position 3 and/or position 8 is replaced with tetrazole, the peptide binds to PAC1R, VPAC1R and VPAC2R, and wherein the modified sequence is a sequence having a deletion or addition of one or more amino acids in the sequence of SEQ ID NO: 3.

[2] The peptide according to [1] above, wherein the neutral amino acids of $X_1$, $X_2$ and $X_3$ are alanine or serine.

[3] The peptide according to [1] or [2] above, wherein the basic amino acids of $X_4$, $X_8$ and $X_9$ are lysine or arginine.

[4] The peptide according to any one of [1] to [3] above, wherein $X_5$ is glutamine, alanine or egTz.

[5] The peptide according to any one of [1] to [4] above, wherein $X_6$ is methionine, norleucine, leucine or alanine.

[6] The peptide according to any one of [1] to [5] above, wherein $X_7$ is valine or alanine.

[7] The peptide according to any one of [1] to [6] above, wherein $X_{10}$ is leucine or alanine.

[8] The peptide according to any one of [1] to [7] above, wherein the carboxy groups of the aspartic acids at position 3 and position 8 of SEQ ID NO: 3 are replaced with tetrazole.

[9] The peptide according to any one of [1] to [8] above, wherein the N-terminus of the peptide is acetylated or mesylated.

[10] The peptide according to any one of [1] to [9] above, wherein the N-terminus of the peptide is acetylated.

[11] The peptide according to any one of [1] to [10] above, wherein one or two amino acids are deleted.

[12] The peptide according to any one of [1] to [11] above, wherein one sequence selected from the group consisting of the following:

GKRYKQRVKNK; (SEQ ID NO: 37)

GKRYKQRVKN; (SEQ ID NO: 38)

GKRYKQRVK; (SEQ ID NO: 39)

GKRYKQRV; (SEQ ID NO: 40)

GKRYKQR; (SEQ ID NO: 41)

GKRYKQ; (SEQ ID NO: 42)

GKRYK; (SEQ ID NO: 43)

GKRY; (SEQ ID NO: 44)

GKR;

GRR;

GK;
and

GR

G;

is added to the C-terminus of the peptide.

[13] A neuroprotective agent containing a peptide according to any one of [1] to [12] above.

[14] A lacrimal secretion promoting agent containing a peptide according to any one of [1] to [12] above.

[15] An anti-inflammatory agent containing a peptide according to any one of [1] to [12] above.

[16] A vascular endothelial function ameliorating agent containing a peptide according to any one of [1] to [12] above.

[17] A corneal epithelial damage treatment agent or corneal endothelial damage treatment agent containing a peptide according to any one of [1] to [12] above.

[18] A dry-eye treatment agent containing a peptide according to any one of [1] to [12] above.

[19] A pharmaceutical composition containing a peptide according to any one of [1] to [12] above.

[20] A method for neuroprotection, lacrimal secretion promotion, vascular endothelial function amelioration or suppression of inflammation, wherein the method includes administering a peptide according to any one of [1] to [12] above.

[21] The peptide according to any one of [1] to [12] above, which is for use in treatment or prevention of nerve disorder, lacrimal fluid reduction disorder, corneal epithelial damage or corneal endothelial damage, inflammatory disease, or dry-eye.

[22] Use of a peptide according to any one of [1] to [12] above for the manufacture of a neuroprotective agent, lacrimal secretion promoting agent, corneal epithelial damage treatment agent, corneal endothelial damage treatment agent, anti-inflammatory agent or dry-eye treatment agent.

Advantageous Effects of Invention

According to the invention it is possible to drastically stabilize PACAP, which has been unstable in aqueous solution.

DESCRIPTION OF EMBODIMENTS

Figure 1:
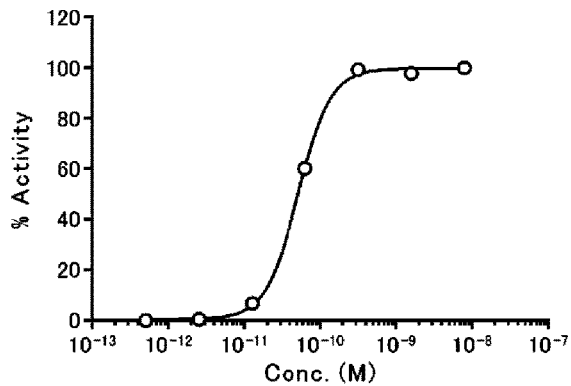
FIG. 1 shows a cAMP inducing effect of different peptides (peptides 1, 2 and 6 to 9) in a PAC1R high-expressing cell line.
Figure 1:
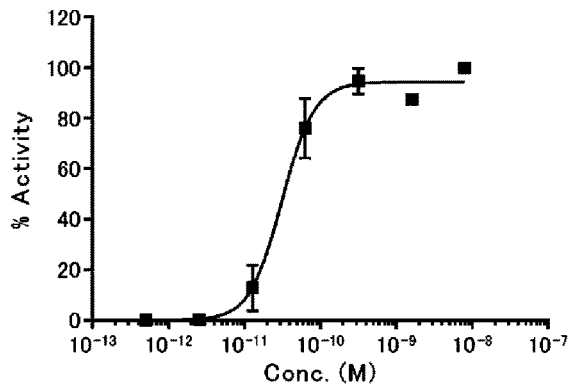
Figure 1:
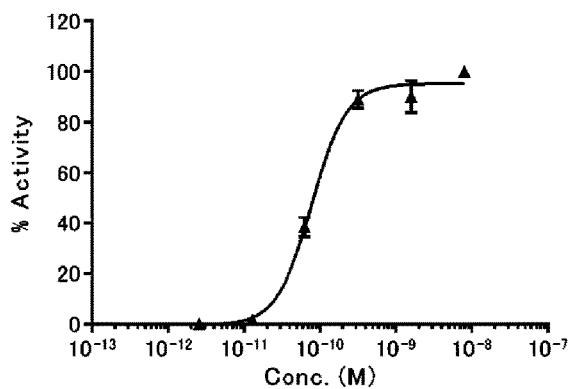
Figure 1:
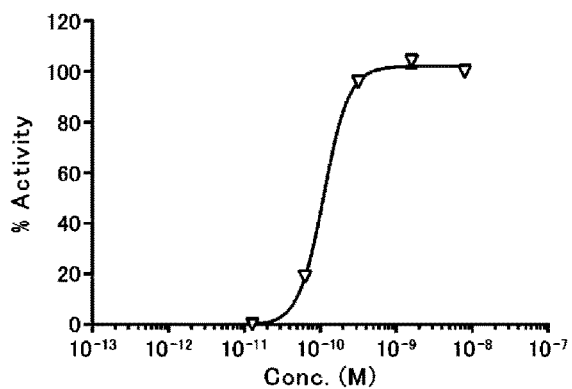
Figure 1:
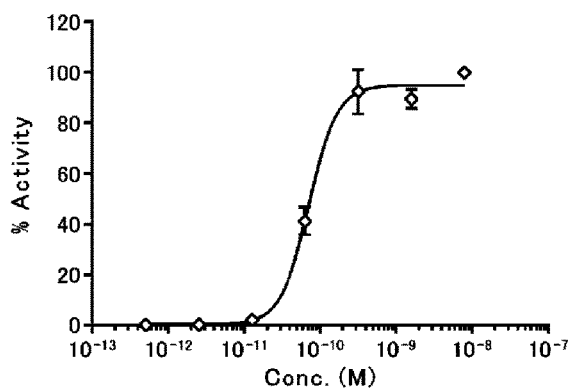
Figure 1:
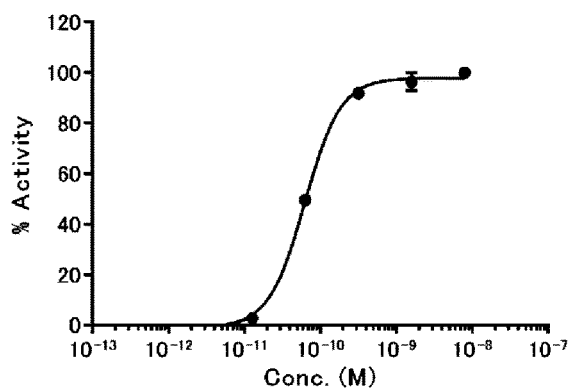

The present invention relates to a peptide consisting of the sequence of PACAP wherein the carboxy groups of the aspartic acid residues at position 3 and/or position 8 are replaced with tetrazole, or its modified sequence. The peptide has an equivalent affinity to PAC1R, VPAC1R and/or VPAC2R with compared to PACAP. The EC50 for these receptors may be within 10-fold, preferably within 5-fold and more preferably within 3-fold compared to PACAP. The PACAP can be either of PACAP38 consisting of 38 residues or PACAP27 consisting of 27 residues. PACAP38 and PACAP27 have the following sequences:

[Chemical Formula 1]

PACAP38:
(SEQ ID NO: 1)
HSDGIFTDSYSRYRKQMAVKKYLAAVLGKRYKQRVKNK

PACAP27:
(SEQ ID NO: 2)
HSDGIFTDSYSRYRKQMAVKKYLAAVL

According to the invention, a "modified sequence" is a sequence in which one or more amino acids of the original sequence have been substituted, deleted or added. More preferably, a "modified sequence" is a sequence in which one or several amino acids of the original sequence have been substituted, deleted or added.

An amino acid substitution may be at any position so long as the affinity of the peptide consisting of the modified sequence for PAC1R, VPAC1R and/or VPAC2R does not change. From the viewpoint of maintaining affinity, the amino acid substitution in the peptide consisting of the modified sequence may be at any position among position 2, position 9, position 11, position 15 to position 17, position 19 to position 21 and position 27 of PACAP27. In a particularly preferred aspect, the amino acids at any of positions $X_1$ to $X_{10}$ in the following sequence:

(SEQ ID NO: 3)
H-$X_1$-D-G-I-F-T-D-$X_2$-Y-$X_3$-R-Y-R-$X_4$-$X_5$-$X_6$-A-$X_7$-$X_8$-

$X_9$-Y-L-A-A-V-$X_{10}$ may be substituted.

The amino acid substitution may be a substitution of one or more amino acids, and from the viewpoint of maintaining activity it may be a substitution of amino acids in any number from 1 to 10, such as 1, 2, 3, 4, 5, 6, 7, 8, 9 or 10. Among them, a substitution of 1 to 4 amino acids are particularly preferable, more preferably 3 amino acids are substituted, even more preferably a 2 amino acids are substituted, and most preferably one amino acid is substituted.

An amino acid deletion may be at any position so long as the affinity of the peptide comprising the modified sequence for PAC1R, VPAC1R and/or VPAC2R does not change. The number of amino acids deleted is selected as any number from 1 to 10, such as 1, 2, 3, 4, 5, 6, 7, 8, 9 or 10. A deletion of one or two amino acids is particularly preferred from the viewpoint of not altering affinity. The amino acid deletion may be a deletion at the N-terminal end or C-terminal end of the original sequence, or a deletion within the sequence. Since PACAP27 and PACAP38 have equivalent binding affinity for PAC1R, VPAC1R and/or VPAC2R, it is believed that deletion of amino acids present at the C-terminal end of PACAP38 have little effect on the affinity.

An amino acid addition may be at any position so long as the affinity of the peptide comprising the modified sequence for PAC1R, VPAC1R and/or VPAC2R does not change. The number of amino acids added is selected as any number from 1 to 10, such as 1, 2, 3, 4, 5, 6, 7, 8, 9 or 10. The amino acids may be added at the N-terminal end or C-terminal end of the original sequence, or they may be added within the sequence. Since PACAP27 and PACAP38 have equivalent binding affinity for PAC1R, VPAC1R and/or VPAC2R, it is believed that addition of any amino acids at the C-terminus of PACAP27 has little effect on the affinity.

One aspect of the invention relates to a peptide consisting of a sequence or modified sequence wherein, in the sequence of the following formula:

(SEQ ID NO: 3)
H-$X_1$-D-G-I-F-T-D-$X_2$-Y-$X_3$-R-Y-R-$X_4$-$X_5$-$X_6$-A-$X_7$-$X_8$-

$X_9$-Y-L-A-A-V-$X_{10}$

{where $X_1$ is a neutral amino acid, $X_2$ is a neutral amino acid, $X_3$ is a neutral amino acid, $X_4$ is a basic amino acid, $X_5$ is a neutral amino acid or egTz, $X_6$ is a non-polar amino acid, $X_7$ is a non-polar amino acid, $X_8$ is a basic amino acid, $X_9$ is a basic amino acid and $X_{10}$ is a non-polar amino acid}, the carboxy group of the aspartic acid residue at position 3 and/or position 8 is replaced with tetrazole, and wherein the peptide has affinity to PAC1R, VPAC1R and/or VPAC2R.

The amino acids represented by $X_1$ to $X_{10}$ may be conservatively substituted with amino acids having the same attributes. Examples of conservative substitutions are substitutions among amino acids in the following groups:
1. Non-polar amino acids: Val, Leu, Ile, Met, Phe, Trp, Pro, Nle, Ala
2. Neutral amino acids: Ala, Ser, Thr, Tyr, Cys, Asn, Gln, Gly
3. Basic amino acid: Lys, Arg, His
4. Acidic amino acids: Asp, Glu A neutral amino acid for $X_1$, $X_2$ and $X_3$ is Ala, Ser, Thr, Tyr, Cys, Asn, Gln or Gly, and more preferably Ala or Ser.

A basic amino acid for $X_4$, $X_8$ and $X_9$ is Lys, Arg or His, and more preferably Lys or Arg.

A neutral amino acid for $X_5$ is Ala, Ser, Thr, Tyr, Cys, Asn, Gln or Gly, and more preferably Ala or Gln. $X_5$ may also be an amino acid having the amide of glutamine replaced with tetrazole (egTz).

A non-polar amino acid for $X_6$ is Val, Leu, Ile, Met, Phe, Trp, Pro, Nle or Ala, and more preferably Met, Nle, Leu or Ala.

A non-polar amino acid for $X_7$ is Val, Leu, Ile, Met, Phe, Trp, Pro, Nle or Ala, and more preferably Val or Ala.

A non-polar amino acid for $X_{10}$ is Val, Leu, Ile, Met, Phe, Trp, Pro, Nle or Ala, and more preferably Leu or Ala.

A modified sequence of the sequence listed as SEQ ID NO: 3, wherein the carboxy groups of the aspartic acid residues at position 3 and/or position 8 have been replaced with tetrazole, is the amino acid sequence represented by SEQ ID NO: 3 with a deletion or addition of one or more amino acids. More preferably, the amino acid sequence represented by SEQ ID NO: 3 may have a deletion of one or two amino acids, or the amino acid sequence represented by SEQ ID NO: 3 may have an addition of the C-terminal added sequence described below.

While it is not intended to be limited by any particular theory, it is presumably because PACAP27 and PACAP38 have equivalent binding affinity for PAC1R, VPAC1R and/or VPAC2R, that addition of any amino acids at the C-terminal end of PACAP27 does not affect the binding affinity for PAC1R. Thus, when the present invention relates to PACAP27, it may include a C-terminal added sequence, or may lack a C-terminal added sequence. The C-terminal added sequence is directed to a sequence consisting of 1 to 11 arbitrary amino acids. The C-terminal added sequence preferably corresponds to the amino acids at position 28 to position 38 of PACAP38. The C-terminal sequences may include following sequences:

GKRYKQRVKNK; (SEQ ID NO: 37)

GKRYKQRVKN; (SEQ ID NO: 38)

GKRYKQRVK; (SEQ ID NO: 39)

GKRYKQRV; (SEQ ID NO: 40)

GKRYKQR; (SEQ ID NO: 41)

(SEQ ID NO: 42)

-continued

GKRYKQ;

GKRYK;                                      (SEQ ID NO: 43)

GKRY                                        (SEQ ID NO: 44)

GKR;

GRR;

GK;
and

GR;

G.

The peptide of the invention may be composed of D-form or L-form amino acids, or non-natural amino acids such as 2-aminoisobutyric acid or L-2-aminoisobutyric acid, so long as the binding affinity for PAC1R, VPAC1R and/or VPAC2R is not lost, and this includes derivatives optionally modified with functional groups at the N-terminal amino group, C-terminal carboxy group or on the amino acid side chain. Examples of modifications include addition of protecting groups on the amino group (for example, acetylation, mesylation, ureidation, carbamation, formylation, Boc-protection or Fmoc-protection), and esterification (such as ethylation) of the carboxy group. It may also include modification that can commonly take place in the body, such as phosphorylation, amidation, methylation, esterification and acetylation, as well as modification that takes place during the synthesis process or that is used to facilitate purification, such as biotinylation. Modification such as PEGylation may also be carried out to extend the in vivo half-life of the peptide. The free amino group of the N-terminal amino acid may be acetylated or mesylated from the viewpoint of increasing stability. In a peptide consisting of a sequence in which the carboxy groups of the aspartic acid residues at position 3 and/or position 8 of PACAP are replaced with tetrazole, the stability can be further increased by acetylation or mesylation of the N-terminus. The C-terminus may be a carboxy group (—COOH), carboxylate (—COO—), amide (—CONH$_2$) or ester (—COOR), and it may also have been glicosylated (see WO2017/027848, for example).

According to one specific aspect, the invention relates to peptides 3 to 34 having the sequences listed in Table 1 below:

TABLE 1

| Peptide name | N-terminus | Sequence | C-terminus |
|---|---|---|---|
| Peptide 1 | H- | HSDGIFTDSYSRYRKQMAVKKYLAAVL (SEQ ID NO: 2) | NH$_2$ |
| Peptide 2 | Ac- | HSDGIFTDSYSRYRKQMAVKKYLAAVL (SEQ ID NO: 4) | NH$_2$ |
| Peptide 3 | H- | HSTzGIFTDSYSRYRKQMAVKKYLAAVL (SEQ ID NO: 5) | NH$_2$ |
| Peptide 4 | H- | HSDGIFTTzSYSRYRKQMAVKKYLAAVL (SEQ ID NO: 6) | NH$_2$ |
| Peptide 5 | H- | HSTzGIFTTzSYSRYRKQMAVKKYLAAVL (SEQ ID NO: 7) | NH$_2$ |
| Peptide 6 | H- | HSTzGIFTTzSYSRYRKQNIAVKKYLAAVL (SEQ ID NO: 8) | NH$_2$ |
| Peptide 7 | H- | HSTzGIFTTzSYSRYRKQLAVKKYLAAVL (SEQ ID NO: 9) | NH$_2$ |
| Peptide 8 | Ac- | HSTzGIFTTzSYSRYRKQNIAVKKYLAAVL (SEQ ID NO: 10) | NH$_2$ |
| Peptide 9 | Ac- | HSTzGIFTTzSYSRYRKQLAVKKYLAAVL (SEQ ID NO: 11) | NH$_2$ |
| Peptide 10 | Ac- | HSTzGIFTTzSYSRYRKQMAVKKYLAAVL (SEQ ID NO: 12) | NH$_2$ |
| Peptide 11 | Ms- | HSTzGIFTTzSYSRYRKQN1AVKKYLAAVL (SEQ ID NO: 13) | NH$_2$ |
| Peptide 12 | Ms- | HSTzGIFTTzSYSRYRKQLAVKKYLAAVL (SEQ ID NO: 14) | NH$_2$ |
| Peptide 13 | Ac- | HSTzGIFTTzSYSRYRKegTzLAVKKYLAAVL (SEQ ID NO: 15) | NH$_2$ |
| Peptide 14 | Ac- | HATzGIFTTzSYSRYRKQLAVKKYLAAVL (SEQ ID NO: 16) | NH$_2$ |
| Peptide 15 | Ac- | HSTzGIFTTzAYSRYRKQLAVKKYLAAVL (SEQ ID NO: 17) | NH$_2$ |
| Peptide 16 | Ac- | HSTzGIFTTzSYARYRKQLAVKKYLAAVL (SEQ ID NO: 18) | NH$_2$ |
| Peptide 17 | Ac- | HSTzGIFTTzSYSRYRKALAVKKYLAAVL (SEQ ID NO: 19) | NH$_2$ |
| Peptide 18 | Ac- | HSTzGIFTTzSYSRYRKQAAVKKYLAAVL (SEQ ID NO: 20) | NH$_2$ |
| Peptide 19 | Ac- | HSTzGIFTTzSYSRYRKQLAAKKYLAAVL (SEQ ID NO: 21) | NH$_2$ |
| Peptide 20 | Ac- | HSTzGIFTTzSYSRYRKQLAVKKYLAAVA (SEQ ID NO: 22) | NH$_2$ |
| Peptide 21 | Ac- | HSTzGIFTTzSYSRYRRQLAVRRYLAAVL (SEQ ID NO: 23) | NH$_2$ |
| Peptide 22 | Ac- | HSTzGIFTTzSYSRYRRQLAVRRYLAAVLGRR (SEQ ID NO: 24) | NH$_2$ |
| Peptide 23 | Ac- | HSTzAIFTTzSYSRYRKQLAVKKYLAAVL (SEQ ID NO: 25) | NH$_2$ |
| Peptide 24 | Ac- | HATzGIFTTzAYSRYRKQLAVKKYLAAVL (SEQ ID NO: 26) | NH$_2$ |

TABLE 1-continued

| Peptide name | N-terminus | Sequence | C-terminus |
|---|---|---|---|
| Peptide 25 | Ac- | HATzGIFTTzSYSRYRKQAAVKKYLAAVL (SEQ ID NO: 27) | NH$_2$ |
| Peptide 26 | Ac- | HSTzGIFTTzAYSRYRKALAVKKYLAAVL (SEQ ID NO: 28) | NH$_2$ |
| Peptide 27 | Ac- | HSTzGIFTTzAYSRYRKQAAVKKYLAAVL (SEQ ID NO: 29) | NH$_2$ |
| Peptide 28 | Ac- | HSTzG1FTTzSYSRYRKAAAVKKYLAAVL (SEQ ID NO: 30) | NH$_2$ |
| Peptide 29 | Ms- | HSTzGIFTTzAYSRYRKQLAVKKYLAAVL (SEQ ID NO: 31) | NH$_2$ |
| Peptide 30 | Ms- | HSTzAIFTTzSYSRYRKQLAVKKYLAAVL (SEQ ID NO: 32) | NH$_2$ |
| Peptide 31 | Ms- | HSTzAIFTTzSYSRYRKQAAVKKYLAAVL (SEQ ID NO: 33) | NH$_2$ |
| Peptide 32 | Ac- | HSTzAIFTTzSYSRYRKQAAVKKYLAAVL (SEQ ID NO: 34) | NH$_2$ |
| Peptide 33 | Ac- | HATzAIFTTzSYSRYRKQAAVKKYLAAVL (SEQ ID NO: 35) | NH$_2$ |
| Peptide 34 | Ac- | HSTzAIFTTzSYSRYRKAAAVKKYLAAVL (SEQ ID NO: 36) | NH$_2$ |

An amino acid in which the carboxy group of aspartic acid has been replaced with tetrazole has the following structure:

[Chemical Formula 2]

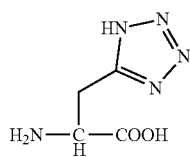

Throughout the present specification, "Tz" will be used as its symbol in the sequences.

An amino acid in which the amide of glutamine has been replaced with tetrazole has the following structure:

[Chemical Formula 3]

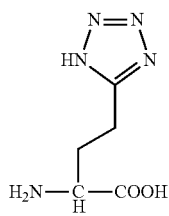

Throughout the present specification, "egTz" will be used as its symbol in the sequences.

The peptide of the invention can be produced by any production method. For example, it can be produced by solid phase synthesis or liquid phase synthesis using the Boc or Fmoc method. In an alternative method, the peptide of the invention can also be produced in host cells by introducing a nucleic acid encoding the peptide of the invention into the host cells, and synthesizeing the peptide in the host cells. In this case, purification after expression can be facilitated by a design in which a tag peptide such as a polyhistidine tag is added at the ends of the peptide.

The peptide of the invention also includes its pharmaceutically acceptable salts. Pharmaceutically acceptable salts include inorganic acid salts (such as hydrochlorides, hydrobromides, sulfates and phosphates), organic acid salts (such as methanesulfonic acid salts, benzenesulfonic acid salts, p-toluenesulfonic acid salts, formic acid salts, acetic acid salts, trifluoroacetic acid salts, oxalic acid salts, citric acid salts, malonic acid salts, fumaric acid salts, maleic acid salts, tartaric acid salts, succinic acid salts and malic acid salts), and salts with bases (such as ammonium salts, methylpyridinium salts and acetylpyridinium salts). The peptide of the invention also includes hydrates or solvates.

Histidine mesylated at the N-terminus can be produced by the method illustrated by reaction formula 1, or a similar method.

[Chemical Formula 4]

Reaction formula 1

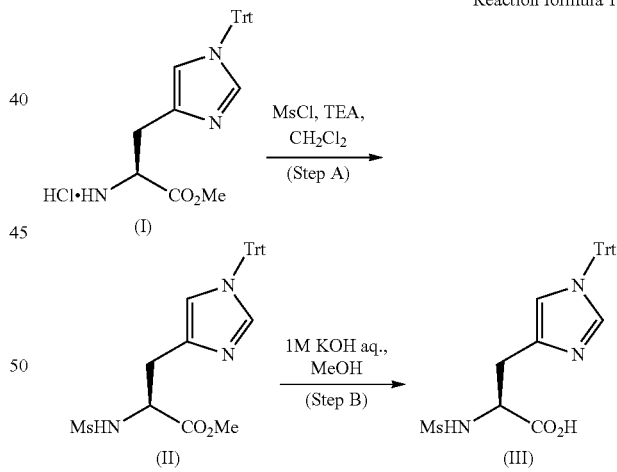

{where Trt represents a trityl group and Me represents a methyl group.}

In the method of reaction formula 1, a compound represented by general formula compound (I) can be reacted with methanesulfonyl chloride in the presence of a base to produce compound (II), after which compound (II) can be subjected to hydrolysis using a base in methanol, to produce compound (III).

For production of compound (II), the base is used at 0.2 to 5 equivalents, preferably 1 to 3 equivalents with respect to compound (I). The base used may be triethylamine, N,N-diisopropylethylamine, pyridine or 4-dimethylaminopyridine, with triethylamine being preferred. Methanesulfonyl chloride is used at 0.1 to 5 equivalents, preferably 1 to 2 equivalents. The solvent is not particularly restricted so long as it does not affect the reaction, and may be tetrahydrofuran, dichloromethane or toluene, for example, with dichloromethane being preferred. The reaction temperature is usually 1° C. to 30° C. and is preferably 15° C. to 25° C., and the reaction time is usually 0.5 hour to 0.12 hours and is preferably 0.5 hour to 2 hours.

For production of compound (III), the base is used at 0.1 to 10 equivalents, preferably 1 to 3 equivalents with respect to compound (II). Bases include lithium hydroxide, sodium hydroxide and potassium hydroxide, preferably potassium hydroxide. The solvent may be a mixed solvent of an organic solvent (such as methanol, ethanol, isopropanol, acetonitrile, 1,4-dioxane or tetrahydrofuran) and water, and is preferably a mixed solvent of methanol and water. The reaction time will differ depending on the reagents or solvent used, but it is usually 0.5 hour to 12 hours, and is preferably 0.5 hour to 3 hours. The reaction temperature will also differ depending on the reagents or solvent, but it is usually 0° C. to 100° C. and is preferably 60° C. to 100° C.

The peptide of the invention can exhibit physiological activity similar to PACAP, by binding with PAC1R, VPAC1R and/or VPAC2R. As an example, the peptide of the invention can exhibit physiological activity as a neuroprotective substance, a nerve regeneration factor, a wound healing promoting factor, an inflammation suppressing factor or an exocrine secretion promoting factor. According to another aspect, therefore, the invention may relate to a neuroprotective agent, a nerve-regenerating agent, a wound healing agent, an anti-inflammatory agent, a corneal epithelial damage treatment agent, a conical endothelial damage treatment agent, a vascular endothelial function ameliorating agent, a dry-eye treatment agent or an exocrine secretion promoting agent, comprising the peptide of the invention. According to yet another aspect, the invention relates to a pharmaceutical composition comprising the peptide of the invention.

The neuroprotective agent of the invention is a drug having neuroprotective action. Therefore, a neuroprotective agent is one that can protect nerves from troubles brought on by nerve cell damage, degeneration and/or death, and may be a neuronal death (apoptosis and/or necrosis) inhibiting agent, a neuronal degeneration inhibiting agent, a neuronal stress reducing agent, a neurocytotoxicity resistance improving agent, a neuronal viability improving agent or an abnormal protein accumulation inhibiting agent.

Throughout the specification, "neuroprotective action" refers to action of protecting nerve cells from their damage, degeneration and/or cell death, and preferably it is action of protecting them from nerve cell death. More specifically, neuroprotective action may include inhibiting nerve cell death (apoptosis and/or necrosis), inhibiting neuronal degeneration, alleviating nerve cell stress, increasing neurocytotoxicity resistance, improving neuron viability, or inhibiting accumulation of abnormal proteins. Nerve cells suffer damage due to physical damage, as well as exposure to neurotoxic substances and lack of oxygen or nutrients, and they can undergo cell death if a certain level of damage is exceeded. Nerve cells also suffer denaturation by accumulation of neurotoxic substances, eventually leading to cell death. Neurotoxic substances are largely classified as exogenous toxic substances or endogenous toxic substances. Exogenous toxic substances include heavy metals, alcohol, and chemical substances such as botulinum toxin. Endogenous toxic substances include active oxygen species, neurotransmitters such as glutamic acid, and abnormal proteins, etc. Neuroprotective action can be easily measured by a person skilled in the art. As an example, nerve cells may be cultured in culture medium containing a test substance (drug group) or culture medium lacking the test substance (control group) under conditions with various types of stress, such as low oxygen load, exposure to neurotoxic substances, nutrient depletion or ultraviolet irradiation, measuring the viable cell count and dead cell count in each culture medium and calculating the percentage of viable cells with respect to the total number of cells, and the test substance can be assessed to have neuroprotective action if the viable cell percentage in the drug group is higher than the viable cell percentage in the control group. In a more preferred method, it can be measured by comparing with a positive control group to which a substance known to have neuroprotective action, such as IGF-1 or NGF, is added, and determining whether or not the test substance has protective action equal to or greater than the positive control group. As another example, the neuroprotective action can be measured by an in vivo animal experiment.

The peptide of the invention has the exocrine gland secretion promoting agent action of PACAP. Since the exocrine gland includes a lacrimal gland or salivary gland, etc., the peptide may be used as an exocrine gland secretion promoting agent such as a lacrimal secretion promoting agent or salivary secretion promoting agent. While it is not intended to be limited to any particular theory, PACAP and the peptide of the invention promote secretion of saliva or lacrimal fluid by binding to receptors (PAC1R, VPAC1R, VPAC2R) expressed on acinar cells of exocrine glands. Since lacrimal fluid covers the surface of the keratoconjunctiva to maintain its wettability, along with smoothing the corneal surface by filling the indentations formed by microvilli on the corneal surface with lacrimal fluid, clear images can be obtained. Epithelial cells of the keratoconjunctiva undergo active metabolism, and when unnecessary cells or metabolites are shed and discharged from the outermost surface, lacrimal fluid flushes them out while supplying the necessary oxygen and nutrients. Lacrimal fluid also flushes out contaminants that have infiltrated the keratoconjunctiva surface, and the bacteriostatic action of lacrimal fluid plays an important role for protection from infection by viruses, bacteria and fungi infiltrating from the outside environment. It also functions as synovial fluid between the eyelids and keratoconjunctiva, for smooth blinking and eye movement. The lacrimal fluid is only a small amount of fluid forming a minute thin-film on the keratoconjunctiva surface, but it is indispensable for maintaining corneal transparency and homeostasis by a variety of elaborate mechanisms. The conditions of an abnormal keratoconjunctiva surface due to disorder in secretion of lacrimal fluid is generally referred to as "dry-eye". When keratoconjunctival damage has occurred due to dry-eye, compounds that promote lacrimal secretion serve as prophylactic and therapeutic agents that are useful for dry-eye and conditions associated with dry-eye. The peptide of the invention can be formulated in an ophthalmic agent, such as eye drop as a lacrimal secretion promoting agent.

The peptide of the invention can also be used as an anti-inflammatory agent, since it has the anti-inflammatory action of PACAP. While it is not intended to be limited to any particular theory, PACAP and the peptide of the invention are able to suppress production of VEGF and inflammatory cytokines (TNF-α, IL-6, IL-12, etc.). In particular, since VPAC1R and VPAC2R, the PACAP receptors, are widely distributed in the gastrointestinal tract and exhibit additional anti-inflammatory action, PACAP and the peptide of the present invention can be used for treatment of inflammatory intestinal diseases.

According to another aspect, the invention relates to a pharmaceutical composition comprising a therapeutically effective dose of the peptide described above. The pharmaceutical composition of the invention can be used for treatment or prevention of a disease that is improved by physiological action of PACAP. Diseases that are improved by physiological action of PACAP include nerve disorder, diseases related to the reduced lacrimal fluid, and inflammatory diseases. The pharmaceutical composition of the invention can treat a disease that is improved by physiological action of PACAP, thorough administration to a patient, or it can prevent the disease through administration to a patient with the potential for developing the disease. Here, "treatment" means that after onset of a disorder or disease, worsening of the condition is prevented, its progression is delayed, or the current condition is maintained, alleviated or reversed, while "prevention" means that onset of a disorder or disease is prevented before onset.

Nerve disorder is a pathological condition where neuronal function is lost due to degeneration or cell death, and it includes cerebral and retinal vascular disorders and neurodegenerative disease.

Vascular disorders include hemorrhagic disorders, such as cerebral hemorrhage and subarachnoid hemorrhage, and cerebrovascular obstruction, such as cerebral thrombus, cerebral infarction and cerebral circulatory insufficiency. Both hemorrhagic disorders and obstructive disorders leave nerve cells in the brain in a state of hypoxia, leading to cell death. Vascular disorders in the retina include hypertensive retinopathy or diabetic retinopathy, central retinal artery occlusion and central retinal vein occlusion, which leave nerve cells in the retina in a state of hypoxia, leading to cell death. Therefore, the peptide, the neuroprotective agent, the vascular endothelial function ameliorating agent or the pharmaceutical composition according to the invention can be administered for the purpose of treatment or prevention of such vascular disorders.

Neurodegenerative diseases include, but are not limited to, degenerative diseases of the central nervous system, such as dementia, Parkinson's disease, spinocerebellar degeneration, Creutzfeldt-Jakob disease, Alzheimer's disease, Huntington's disease, multiple sclerosis, mad cow disease and epilepsy, motor neurodegenerative diseases such as spontaneous progressive muscular atrophy, amyotrophic lateral sclerosis and spinal-bulbar muscular atrophy, and sensory neurodegenerative diseases. Sensory neurodegenerative diseases include, but are not limited to, degenerative diseases of visual, auditory, tactile, gustatory and olfactory nerves, with visual degenerative diseases including glaucoma, retinitis pigmentosa, age-related macular degeneration and diabetic retinopathy, and auditory neurodegenerative diseases including hearing impairment.

Diseases related to the reduced lacrimal fluid include, but are not limited to, dry-eye, keratoconjunctivitis sicca and reduced lacrimation, etc.

Corneal epithelial damage is a condition that occurs when corneal epithelial cell proliferation is suppressed, or epithelial shedding is enhanced, thereby leading to an imbalance in epithelial homeostasis. Corneal epithelial damage means corneal epithelial damage caused by intrinsic disease factors such as corneal ulcer, corneal epithelial detachment, diabetic keratopathy, keratoconjunctivitis sicca, chronic superficial keratitis, superficial punctate keratopathy, corneal erosion and protracted corneal epithelial loss, extrinsic diseases factors such as drugs, trauma or contact lens usage, or physical or chemical injury.

Dry-eye is a chronic disease related to lacrimal fluid and the conjunctival epithelium due to a variety of factors, and it is accompanied by eye discomfort and visual function abnormalities. Lacrimal fluid abnormalities include the quantitative abnormality of reduced lacrimal fluid flow, and the qualitative abnormality of change in lacrimal fluid quality or ability to retain lacrimal fluid. Dry-eye also includes the dry-eye that accompanies reduced lacrimation, lacrimal fluid-evaporative dry eye and Sjogren's syndrome, Stevens-Johnson syndrome, conical epithelial erosion, blepharitis, ophthalmic pemphigus, vernal conjunctivitis, allergic conjunctivitis and vitamin A deficiency.

Inflammatory diseases include, but are not limited to, asthma, atopic dermatitis, hives, pollen hypersensitivity, anaphylactic shock, sinusitis (including eosinophilic sinusitis), rheumatism, multiple sclerosis; arthritis, systemic lupus erythematosus, psoriasis, ankylosing spondylitis, inflammatory intestinal disease (for example, ulcerative colitis, Crohn disease and gluten-sensitive intestinal disease), Sjogren's syndrome, chronic graft-versus-host disease (GVHD), corneal infectious disease, allergic conjunctivitis, corneal trauma, polymyositis, dermatomyositis, myasthenia gravis, chronic obstructive pulmonary disease (COPD) and dermatosclerosis.

Corneal endothelial damage includes damage related to Fuchs corneal endothelial dystrophy, persistent decreased corneal endothelial density following conical transplantation, trauma, ophthalmologic surgery, aging and corneal endothelitis.

Diseases known to be associated with vascular endothelial cellular damage include, but are not limited to, diabetes, hypertension and atherosclerosis.

The peptide of the invention, or a neuroprotective agent, nerve-regenerating agent, anti-inflammatory agent, wound healing promoting agent or exocrine gland secretion promoting agent, or the pharmaceutical composition comprising the peptide, may be administered parenterally or orally, depending on the disease to be treated. Oral administration may be sublingual, intraoral or oral administration. Examples of parenteral administration include administration by intravenous, intraarterial, subcutaneous, local, intraperitoneal, intramuscular, nasal, transdermal, transmucosal, intrameningeal, perrectal, intramuscular, intracerebral, intrameningeal, subarachnoid, intradural, epidural, eye drop, ear drop, nasal drop or intraocular routes. Intraocular routes include, more specifically, subconjunctival, sub-Tenon and intravitreal routes. A pharmaceutical composition containing the peptide of the invention may be prepared in an appropriate dosage form for the route of administration, and may be an eye drop, injection, powdered drug, infusion preparation, granules, tablets or suppository, for example, but for parenteral administration it is preferably an eye drop, injection, infusion preparation, or a powdered drug for preparation prior to use. A formulation for intraocular administration include, for example, an intravitreal injection, subconjunctival injection or sub-Tenon injection. Such formulations may also contain various pharmaceutically acceptable adjuvants, i.e. carriers or other auxiliary agents, for example additives including stabilizers, antiseptic agents, soothing agents and emulsifiers, etc. They may also be used in combination with other drugs that have neuroprotective effects, inflammation-suppressing effects or exocrine gland secretion effects.

All of the publications mentioned throughout the present specification are incorporated herein in their entirety by reference.

The examples of the invention described below are intended for exemplification only, and do not limit the technical scope of the invention. The technical scope of the invention is limited solely by the description in the Claims. It is possible to modify the invention, for example, to add, delete or substitute the constituent features of the invention, as so long as the gist of the invention is maintained.

EXAMPLES

Example 1: Peptide Synthesis 1

Synthesis of Ms-His(Trt)-OMe

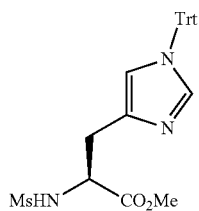

[Chemical Formula 5]

To a dichloromethane solution (15 mL) containing N-imtrityl-L-histidine methyl ester hydrochloride (2.02 g, 4.5 mmol), triethylamine (1.0 mL, 7.2 mmol) and a dichloromethane solution (1.0 mL) containing methanesulfonyl chloride (326.8 mg, 2.9 mmol) was added, and the mixture was stirred at room temperature for 1 hour. A saturated sodium hydrogencarbonate aqueous solution was then added to stop the reaction, extraction was performed with ethyl acetate, the obtained organic layer was washed with a 10% citric acid aqueous solution, saturated sodium hydrogencarbonate aqueous solution and saturated saline solution, the organic layer was dried over anhydrous sodium sulfate, and the solvent was distilled off under reduced pressure to obtain a pale yellow solid (2.35 g, >100%). The obtained solid was used in the following reaction without purification.

$^1$H-NMR (400 MHz, CDCl$_3$) δ 7.38 (1H, d, J=1.2 Hz), 7.34-7.31 (9H, m), 7.12-7.08 (6H, m), 6.57 (1H, d, J=2.4 Hz), 6.30 (1H, d, J=8.4 Hz), 4.40 (1H, dt, =8.4, 5.2 Hz), 3.65 (3H, s), 3.05 (2H, d, J=5.2 Hz), 2.97 (3H s).

Synthesis of Ms-His(Trt)-OH

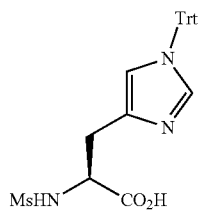

[Chemical Formula 6]

To a methanol solution (15 mL) containing Ms-His-OMe (2.21 g, 4.5 mmol), 1 M potassium hydroxide aqueous solution (9.0 mL, 9.0 mmol) was added, and the mixture was refluxed for 1.5 hours. The reaction mixture was cooled to room temperature, acidified to pH 5 with a 10% citric acid aqueous solution, and extracted with dichloromethane. The obtained organic layer was dried over sodium sulfate and the solution was distilled off under reduced pressure, after which dichloromethane and hexane were added to the residue to precipitate a white solid, which was filtered (2.32 g, >100%). $^1$H-NMR (400 MHz, CDCl$_3$) δ 7.84 (1H, s), 7.31-7.33 (9H, m), 7.12-7.09 (6H, in), 6.82 (1H, s), 4.13 (1H, m), 3.34 (1H, dd, J=14.8, 3.6 Hz), 3.17 (1H, dd, J=14.8, 6.8 Hz), 2.90 (3H, s).

Example 2: Peptide Synthesis 2

The peptides used in the test were synthesized by solid phase synthesis utilizing the Fmoc method by means of a peptide synthesizer (model: PSSM-8 by Shimadzu Corp.). The non-natural amino acids used in the solid phase synthesis, i.e., Fmoc-TZ-OH, Fmoc-TZ (trt)-OH and Fmoc-egTZ (trt)-OH, were purchased from Astatech Inc. Peptides 1 to 34 of the following sequences were synthesized, and the molecular weights of the synthetic peptides were subjected to mass spectrometry (MALD1 TOF). As shown in Table 2, all of the measured values matched theoretical values.

TABLE 2

| Peptide name | N-terminus | Sequence | C-terminus | Calculated | Found |
|---|---|---|---|---|---|
| Peptide 1 | H- | HSDGIFTDSYSRYRKQMAVKKYLAAVL (SEQ ID NO: 2) | NH$_2$ | 3146.66 | 3147.0 |
| Peptide 2 | Ac- | HSDGIFTDSYSRVRKQMAVKKYLAAVL (SEQ ID NO: 4) | NH$_2$ | 3188.67 | 3188.4 |
| Peptide 3 | H- | HSTzGIFTDSYSRYRKQMAVKKYLAAVL (SEQ 10 NO: 5) | NH$_2$ | 3170.68 | 3171.1 |
| Peptide 4 | H- | HSDGIFTTzSYSRYRKQMAVKKYLAAVL (SEQ ID NO: 6) | NH$_2$ | 3170.68 | 3170.8 |
| Peptide 5 | H- | HSTzGIFTTzSYSRYRKQMAVKKYLAAVL (SEQ ID NO: 7) | NH$_2$ | 3194.70 | 3194.2 |
| Peptide 6 | H- | HSTzGIFTTzSYSRYRKQNIAVKKYLAAVL (SEQ ID NO: 8) | NH$_2$ | 3176.75 | 3177.0 |
| Peptide 7 | H- | HSTzGIFTTzSYSWYRKQLAVKKYLAAVL (SEQ ID NO: 9) | NH$_2$ | 3176.75 | 3176.9 |
| Peptide 8 | Ac- | HSTzGIFFTzSYSRYRKQNIAVKKYLAAVL (SEQ ID NO: 10) | NH$_2$ | 3218.76 | 3219.2 |
| Peptide 9 | Ac- | HSTzGIFTTzSYSRYRKQLAVKKYLAAVL (SEQ ID NO: 11) | NH$_2$ | 3218.76 | 3218.2 |
| Peptide 10 | Ac- | HSTzGIFTTzSYSRYRKQMAVKKYLAAVL (SEQ ID NO: 12) | NH$_2$ | 3236.71 | 3236.7 |
| Peptide 11 | Ms- | HSTzGIFTTzSYSRYRKQNIAVKKYLAAVL (SEQ ID NO: 13) | NH$_2$ | 3254.72 | 3255.0 |

TABLE 2-continued

| Peptide name | N-terminus | Sequence | C-terminus | Calculated | Found |
|---|---|---|---|---|---|
| Peptide 12 | Ms- | HSTzGIFTTzSYSRYKKQLAVKKYLAAVL (SEQ ID NO: 14) | $NH_2$ | 3254.72 | 3254.4 |
| Peptide 13 | Ac- | HSTzGIFTTzSYSRYRKegTzLAVKKYLAAVL (SEQ ID NO: 15) | $NH_2$ | 3243.76 | 3243.7 |
| Peptide 14 | Ac- | HATzGIFTTzSYSKYRKQLAVKKYLAAVL (SEQ ID NO: 16) | $NH_2$ | 3202.76 | 3202.8 |
| Peptide 15 | Ac- | HSTzGIFTTzSYSRYRKQLAVKKYLAAVL (SEQ ID NO: 17) | $NH_2$ | 3202.76 | 3202.4 |
| Peptide 16 | Ac- | HSTzGIFTTzSYARYRKQLAVKKYLAAVL (SEQ ID NO: 18) | $NH_2$ | 3202.76 | 3202.8 |
| Peptide 17 | Ac- | HSTzGIFTTzSYSRYRKALAVKKYLAAVL (SEQ ID NO: 19) | $NH_2$ | 3161.73 | 3161.4 |
| Peptide 18 | Ac- | HSTzGIFTTzSYSRYRKQAAVKKYLAAVL (SEQ ID NO: 20) | $NH_2$ | 3176.71 | 3176.6 |
| Peptide 19 | Ac- | HSTzGIFTTzSYSRYRKQLAAKKYLAAVL (SEQ ID NO: 21) | $NH_2$ | 3190.72 | 3190.2 |
| Peptide 20 | Ac- | HSTzGIFTTzSYSRYRKQLAVKKYLAAVA (SEQ ID NO: 22) | $NH_2$ | 3176.71 | 3176.4 |
| Peptide 21 | Ac- | HSTzGIFTTzSYSRYRRQLAVRRYLAAVL (SEQ ID NO: 23) | $NH_2$ | 3302.71 | 3303.1 |
| Peptide 22 | Ac- | HSTzGIFTTzSYSRYRRQLAVRRYLAAVLGRR (SEQ ID NO: 24) | $NH_2$ | 3672.00 | 3672.5 |
| Peptide 23 | Ac- | HSTzGIFTTzSYSRYRKQLAVKKYLAAVL (SEQ ID NO: 25) | $NH_2$ | 3232.77 | 3232.8 |
| Peptide 24 | Ac- | HATzGIFTTzAYSRYRKQLAVKKYLAAVL (SEQ ID NO: 26) | $NH_2$ | 3186.77 | 3186.3 |
| Peptide 25 | Ac- | HATzGIFTTzSYSRYRKQAAVKKYLAAVL (SEQ ID NO: 27) | $NH_2$ | 3160.72 | 3160.2 |
| Peptide 26 | Ac- | HSTzGIFTTzAYSRYRKALAVKKYLAAVL (SEQ ID NO: 28) | $NH_2$ | 3145.74 | 3145.3 |
| Peptide 27 | Ac- | HSTzGIFTTzAYSRYRKQAAVKKYLAAVL (SEQ ID NO: 29) | $NH_2$ | 3160.71 | 3160.3 |
| Peptide 28 | Ac- | HSTzGIFTTzSYSRYRKAAAVKKYLAAVL (SEQ ID NO: 30) | $NH_2$ | 3119.69 | 3119.3 |
| Peptide 29 | Ms- | HSTzGIFTTzAYSRYRKQLAVKKYLAAVL (SEQ ID NO: 31) | $NH_2$ | 3238.73 | 3238.7 |
| Peptide 30 | Ms- | HSTzAIFTTzSYSRYRKQLAVKKYLAAVL (SEQ ID NO: 32) | $NH_2$ | 3268.74 | 3268.6 |
| Peptide Si | Ms- | HSTzAIFTTzSYSRYRKQAAVKKYLAAVL (SEQ ID NO: 33) | $NH_2$ | 3226.69 | 3226.3 |
| Peptide 32 | Ac- | HSTzAIFTTzSYSRYRKQAAVKKYLAAVL (SEQ ID NO: 34) | $NH_2$ | 3190.72 | 3191.1 |
| Peptide 33 | Ac- | HATzAIFTTzSYSKYRKQAAVKKYLAAVL (SEQ ID NO. 35) | $NH_2$ | 3174.73 | 3174.4 |
| Peptide 34 | Ac- | HSTzAIFTTzSYSRYRKAAAVKKYLAAVL (SEQ ID NO: 36) | $NH_2$ | 3133.70 | 3134.0 |

Example 3: Peptide Stability Test 1

Preparation of Measuring Sample

Peptides 1 and 3 to 5 synthesized in Example 2 were weighed and dissolved in phosphate buffer (pH 7.0) to prepare 1.0 mM peptide solutions. The 1.0 mM peptide solutions were then diluted with phosphate buffer to 100 μM. After filtering with. Chromatdisk (product of Merck Millipore, Millex-GV, 0.22 μm), each filtrate was dispensed into an LC vial (Waters Deactivated Qsert Vial). The prepared peptide solutions were incubated for one month or 2 months in a 40° C. thermostatic bath to obtain stored samples. A simultaneously prepared sample among the peptide solutions that was not stored was used as a standard sample (initial sample). The standard sample and the stored samples were stored at −30° C. until sample analysis.

Moisture Permeability

Using the total weight of the aqueous peptide solution and storage vessel as the specimen weight, measurements were recorded as the specimen weights before storage and the specimen weights after storage under different storage conditions. The empty weight of the storage vessel was also measured, and the moisture permeability was determined by the following formula.

[Mathematical Formula 1]

$$\text{Moisture permeability of vessel (\%)} = \frac{\text{(Specimen weight before storage (g)} - \text{specimen weight after storage (g))}}{\text{(Specimen weight before storage (g)} - \text{storage vessel weight (g))}} \times 100$$

After stirring the standard sample and the stored samples on a vortex mixer, each peptide solution was transferred to an HPLC vial (Deactivated Qsert vial by Waters Co.). Reverse-phase HPLC (HPLC system: Prominence by Shimadzu Corp.) was conducted under the conditions shown in Table 3 below for analysis of the peptide solutions, and chromatograms were obtained.

HPLC Analysis Conditions 1

Column: XSelect CSH C18 by Waters Co., 5 μm, 4.6×250 mm
Guard column: XSelect CSH C18 by Waters. Co., 5 μm, 4.6×20 mm Guard Cartridge
Detection wavelength: 220 nm
Mobile phase A: 0.1% formic acid in water
Mobile phase B: 0.1% formic acid in acetonitrile
Measuring time: 30 minutes
Measuring sample injection rate: 50 μL
Flow rate: 1.0 ml/min
Sample cooler: 4° C.
Column temperature: 40° C.
Mobile phase delivery: The mixing ratio of mobile phase A and mobile phase B was varied as shown in Table 3 for linear concentration gradient control.

TABLE 3

| Time after sample injection (min) | Mobile phase A (vol %) | Mobile phase B (vol %) |
|---|---|---|
| 0-30.0 | 90 → 75 | 10 → 25 |
| 30.0-30.5 | 75 → 0 | 25 → 100 |
| 30.5-36.5 | 0 | 100 |
| 36.5-37.0 | 0 → 90 | 100 → 10 |
| 37.0-49.5 | 90 | 10 |

The peak area value for the peptide in the chromatogram was calculated, and the survival rate (survival rate before correction for water) was calculated using formula (2). The survival rate after correction for water was also calculated from the survival rate before correction for water using formula (3), taking into account the moisture permeability of the container.

[Mathematical Formula 2]

$$\text{Survival rate before correction for water (\%)} = \frac{\text{Peak area value for peptide in stored sample}}{\text{Peak area value for peptide in standard sample}} \times 100 \quad (2)$$

[Mathematical Formula 3]

$$\text{Survival rate after correction for water (\%)} = \frac{(\text{Survival rate before correction for water (\%)}) \times (100 - \text{moisture permability of container (\%)})}{100} \quad (3)$$

Table 4 shows the survival rate after correction for water for each peptide among the stored samples.

TABLE 4

| Peptide No. | 40° C., 1-month storage | 40° C., 2-month storage |
|---|---|---|
| Peptide 1 | 37.4% | 21.3% |
| Peptide 3 | 76.5% | 60.7% |
| Peptide 4 | 42.8% | 28.2% |
| Peptide 5 | 94.7% | 85.6% |

Peptide 1 (PACAP) had low stability, leaving 37.4% after storage at 40° C. for one month and 21.3% after storage at 40° C. for 2 months. Peptide 3, which had only the carboxy group of the aspartic acid side chain at the 3rd residue of peptide 1 replaced with tetrazole, exhibited higher stability than peptide 1, while peptide 4, which had only the carboxy group of the aspartic acid side chain at the 8th residue replaced with tetrazole, also had increased stability compared to peptide 1, However, peptide 5, which had the carboxy groups of the aspartic acid side chains of the 3rd and 8th residues of peptide 1 replaced with tetrazole, had further increased stability over peptide 3 and peptide 4, thus demonstrating that for increased PACAP stability it is more effective to have two tetrazole substitutions than a single tetrazole substitution.

Example 4: Peptide Stability Test 2

Peptides 1, 2 and 6 to 9 synthesized in Example 2 were weighed and dissolved in Tris buffer (pH 7.0) to prepare 1.0 mM peptide solutions. The solutions were filtered with a Chromatdisk (product of Merck Millipore, Millex-GV, 0.22 μm). Each filtrate was diluted to 100 μM with Tris buffer (pH 7.0) and dispensed into a tube (Protein LoBind Tube by Eppendorf Co.). The prepared peptide solutions were incubated for 1 week or 2 weeks in a 60° C. thermostatic bath to obtain stored samples. A simultaneously prepared sample among the peptide solutions that was not stored was used as a standard sample (initial sample). The standard sample and the stored samples were stored at −30° C. until sample analysis.

Each stored sample was measured under the following HPLC analysis conditions 2, and the survival rate after correction for water for each peptide among the stored samples was calculated in the same manner as Example 3. The results are shown in Table 6.

HPLC Analysis Conditions 2

Column: XSelect CSH C18 by Waters Co., 5 μm, 4.6×250 mm
Guard column: XSelect CSH C18 by Waters. Co., 5 μm, 4.6×20 mm Guard Cartridge
Detection wavelength: 220 nm
Mobile phase A: 0.1% formic acid in water
Mobile phase B: 0.1% formic acid in acetonitrile
Measuring time: 20 minutes
Measuring sample injection rate: 50 μL
Flow rate: 1.0 mL/min
Column temperature: 40° C.
Sample cooler: 25° C.
Mobile phase delivery: The mixing ratio of mobile phase A and mobile phase B was varied as shown in Table 5 for linear concentration gradient control.

TABLE 5

| Time after sample injection (min) | Mobile phase A (vol %) | Mobile phase B (vol %) |
|---|---|---|
| 0-20.0 | 85 → 75 | 15 → 25 |
| 20.0-20.1 | 75 → 0 | 25 → 100 |
| 20.1-24.5 | 0 | 100 |
| 24.5-25.0 | 0 → 85 | 100 → 15 |
| 25.0-40.0 | 85 | 15 |

TABLE 6

| Peptide No. | 60° C., 1-week storage | 60° C., 2-week storage |
| --- | --- | --- |
| Peptide 1 | 26.6% | 15.8% |
| Peptide 2 | 28.7% | 17.2% |
| Peptide 6 | 91.3% | 82.4% |
| Peptide 7 | 91.7% | 84.8% |
| Peptide 8 | 98.1% | 92.9% |
| Peptide 9 | 98.4% | 92.8% |

Peptide 1 (PACAP) had very poor stability, leaving 26.6% after storage for 1 week at 60° C. and 15.8% after storage for 2 weeks, while peptide 2, which had the N-terminus of PACAP acetylated, exhibited only equivalent stability. Peptides 6 and 7, on the other hand, which had the carboxy groups of the aspartic acids at position 3 and position 8 replaced with tetrazole (peptide 6 also having the methionine at position 17 replaced with norleucine (indicated as "N1" in the sequence) and peptide 7 further having the methionine at position 17 replaced with leucine), had drastically increased stability, leaving 91.3% and 91.7% after storage for 1 week at 60° C., and 82.4% and 84.8% after storage for 2 weeks. Peptide 8 and 9, which had the N-termini of peptides 6 and 7 acetylated, had further increased stability, leaving 98.1% and 98.4% after storage for 1 week at 60° C., and 92.9% and 92.8% after storage for 2 weeks. An accelerated test for 1 week and 2 weeks at 60° C. corresponds respectively to approximately 1 year and 2 years at room temperature (25° C.). Therefore, peptides 8 and 9 are expected to be stable (survival rate of 90% or higher) for 2 years at room temperature.

Example 5: Peptide Stability Test 3

Peptides 12 to 25, 27 and 28 synthesized in Example 2 were weighed and dissolved in Tris buffer (pH 7.0) to prepare 1.0 mM peptide solutions. The solutions were filtered with a Chromatdisk (product of Merck Millipore, Millex-GV, 0.22 μm). Each filtrate was diluted to 100 μM with Tris buffer (pH 7.0) and dispensed into a tube (Protein LoBind Tube by Eppendorf Co.). The prepared peptide solutions were incubated for one week or 2 weeks in a 60° C. thermostatic bath to obtain stored samples. A simultaneously prepared sample among the peptide solutions that was not stored was used as a standard sample (initial sample). The standard sample and the stored samples were stored at −30° C. until sample analysis.

The survival rate after correction for water for each peptide among the stored samples was calculated in the same manner as Example 4, and the results are shown in Table 7.

TABLE 7

| Peptide No. | 60° C., 1-week storage | 60° C., 2-week storage |
| --- | --- | --- |
| Peptide 12 | 97.0% | 93.6% |
| Peptide 13 | 97.4% | 95.4% |
| Peptide 14 | 96.7% | 94.5% |
| Peptide 15 | 97.3% | 94.9% |
| Peptide 16 | 98.1% | 93.5% |
| Peptide 17 | 97.8% | 93.4% |
| Peptide 18 | 96.7% | 90.6% |
| Peptide 19 | 95.8% | 92.7% |
| Peptide 20 | 93.9% | 91.8% |
| Peptide 21 | 97.8% | 93.5% |
| Peptide 22 | 98.2% | Not measured |

TABLE 7-continued

| Peptide No. | 60° C., 1-week storage | 60° C., 2-week storage |
| --- | --- | --- |
| Peptide 23 | 96.5% | 93.1% |
| Peptide 24 | 98.1% | 94.3% |
| Peptide 25 | 95.8% | 91.2% |
| Peptide 27 | 96.4% | 93.5% |
| Peptide 28 | 94.6% | 90.5% |

Peptide 12 (a peptide having the N-terminal acetyl group of peptide 9 replaced with a mesyl group) exhibited similar stability to peptide 9, and therefore high stability was exhibited even with N-terminal mesyl group substitution. Peptide 13 (a peptide having the glutamine side chain of the 16th residue of peptide 9 replaced with tetrazole) exhibited similar stability to peptide 9, indicating that high stability is maintained even with a peptide having the glutamine side chain replaced with tetrazole. High stability was also maintained with peptides 14 to 25, peptide 27 and peptide 28, which had alanine or arginine substituting or added at arbitrary residues of peptide 9.

Example 5-2: Peptide Stability Test 3

Peptides 29 to 34 synthesized in Example 2 were weighed and dissolved in Tris buffer (pH 7.0) to prepare 1.0 mM peptide solutions. The solutions were filtered with a Chromatdisk (product of Merck Millipore, Millex-GV, 0.22 μm). Each filtrate was diluted to 100 μM with Tris buffer (pH 7.0) and dispensed into a tube (Protein LoBind Tube by Eppendorf Co.). The prepared peptide solutions were incubated for 2 weeks in a 60° C. thermostatic bath to obtain stored samples. A simultaneously prepared sample among the peptide solutions that was not stored was used as a standard sample (initial sample). The standard sample and the stored samples were stored at −30° C. until sample analysis.

The survival rate after correction for water for each peptide among the stored samples was calculated in the same manner as Example 4, and the results are shown in Table 7-2.

TABLE 7-2

| Peptide No. | 60° C., 2-week storage |
| --- | --- |
| Peptide 29 | 91.9 |
| Peptide 30 | 92.2 |
| Peptide 31 | 90.1 |
| Peptide 32 | 88.7 |
| Peptide 33 | 85.3 |
| Peptide 34 | 96.9 |

Peptide 29 (a peptide having the N-terminal acetyl group of peptide 15 replaced with a mesyl group) exhibited similar stability to peptide 15, and therefore high stability was exhibited even with N-terminal mesyl group substitution. Peptide 30 (a peptide having the N-terminal acetyl group of peptide 23 replaced with a mesyl group) exhibited similar stability to peptide 23, and therefore high stability was exhibited even with N-terminal mesyl group substitution. High stability was also maintained with peptides 32 to 34, which had alanine substituting at arbitrary residues of peptide 9. Peptide 31 (a peptide having the N-terminal acetyl group of peptide 32 replaced with a mesyl group) exhibited similar stability to peptide 32.

Example 6: Peptide Stability Test 4

Peptides 10 and 11 synthesized in Example 2 were weighed and dissolved in phosphate buffer (pH 7.0) to prepare 1.0 mM peptide solutions. The solutions were filtered with a Chromatdisk (product of Merck Millipore, Millex-GV, 0.22 Each filtrate was diluted to 100 μM with phosphate buffer (pH 7.0) and dispensed into a tube (Protein LoBind Tube by Eppendorf Co.). The prepared peptides were incubated for one month or 2 months in a 40° C. thermostatic bath to obtain stored samples. A simultaneously prepared sample among the peptide solutions that was not stored was used as a standard sample (initial sample). The standard sample and the stored samples were stored at −30° C. until sample analysis.

The survival rate after correction for water for each peptide among the stored samples was measured in the same manner as Example 4, and the results are shown in Table 8.

TABLE 8

| Peptide No. | 40° C., 1-month storage | 40° C., 2-month storage |
|---|---|---|
| Peptide 10 | 94.0% | 87.8% |
| Peptide 11 | 94.2% | 88.8% |

The results for peptide 10 having an N-terminal acetyl group and peptide 11 having a N-mesyl group demonstrated that the peptide is stabilized to the same degree whether the N-terminal substituent is an acetyl group or an N-mesyl group.

Example 7: Peptide Stability Test 5

Peptide 26 synthesized in Example 2 was weighed and dissolved in Tris buffer (pH 7.0) to prepare 1.0 mM peptide solutions. Each solution was filtered with a Chromatdisk (product of Merck Millipore, Millex-GV, 0.22 μm). The filtrate was diluted to 100 μM with Tris buffer (pH 7.0) and dispensed into a tube (Protein LoBind Tube by Eppendorf Co.). The prepared peptide solutions were incubated for one week or 2 weeks in a 60° C. thermostatic bath to obtain stored samples. A simultaneously prepared sample among the peptide solutions that was not stored was used as a standard sample (initial sample). The standard sample and the stored samples were stored at −30° C. until sample analysis.

The stored sample was measured under the following HPLC analysis conditions 3, and the survival rate after correction for water for the peptide among the stored samples was calculated in the same manner as Example 3. The results are shown in Table 10.

HPLC Analysis Conditions 3

Column: XSelect CSH C18 by Waters Co., 5 μm, 4.6×250 mm
Guard column: XSelect CSH C18 by Waters Co., 5 4.6×20 mm Guard Cartridge
Detection wavelength: 220 nm
Mobile phase A: 0.1% formic acid in water
Mobile phase B: 0.1% formic acid in acetonitrile
Measuring time: 20 minutes
Measuring sample injection volume: 50 μL
Flow rate: 1.0 mL/min
Column temperature: 40° C.
Sample cooler: 25° C.

Mobile phase delivery: The mixing ratio of mobile phase A and mobile phase B was varied as shown in Table 9 for linear concentration gradient control.

TABLE 9

| Time after sample injection (min) | Mobile phase A (vol %) | Mobile phase B (vol %) |
|---|---|---|
| 0-20.0 | 82.5 → 72.5 | 17.5 → 27.5 |
| 20.0-20.1 | 72.5 → 0 | 27.5 → 100 |
| 20.1-24.5 | 0 | 100 |
| 24.5-25.0 | 0 → 82.5 | 100 → 17.5 |
| 25.0-40.0 | 82.5 | 17.5 |

TABLE 10

| Peptide No. | 60° C., 1-week storage | 60° C., 2-week storage |
|---|---|---|
| Peptide 26 | 98.0% | 94.8% |

Peptide 26 exhibited similar high stability.

Example 7: cAMP Assay of PACAP27 and its Modified Peptide

Cell Culture

CHO-K1 cells (PAC1 or VPAC1 receptor high-expressing cell line: purchased from DiscoveRx Co.) that had been mitomycin-treated and frozen were prepared with Cell plating reagent (product of DiscoveRx) at $1.35 \times 10^4$ cells/100 μl/well, and then seeded in a 96-well culture plate. The cells were cultured for 18 to 24 hours at 37° C. in a 5% $CO_2$ incubator, adhering the cells to the plate.

Reagent Preparation

Powders of peptides 1, 2 and 6 to 9 synthesized in Example 2 were dissolved in water to 0.1 mM, and then diluted to 20 μM with Cell assay buffer (DiscoveRx) (containing 0.5 mM IBMX and 0.001% BSA). A 5-fold dilution series was then prepared with the same Cell assay buffer and used in an assay.

cAMP Assay

Figure 2:
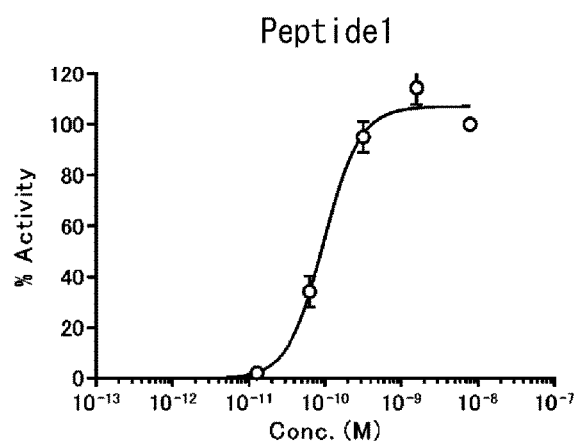
FIG. 2 shows a cAMP inducing effect of different peptides (peptides 1, 2 and 6 to 9) in a VPAC1R high-expressing cell line.
Figure 2:
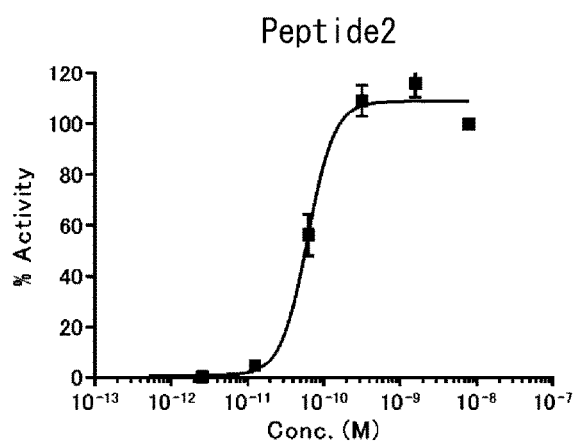
Figure 2:
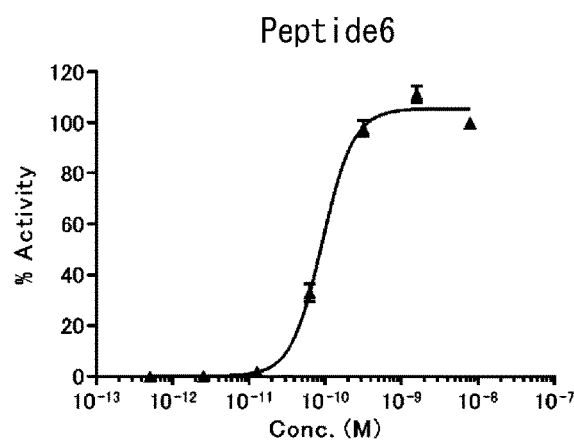
Figure 2:
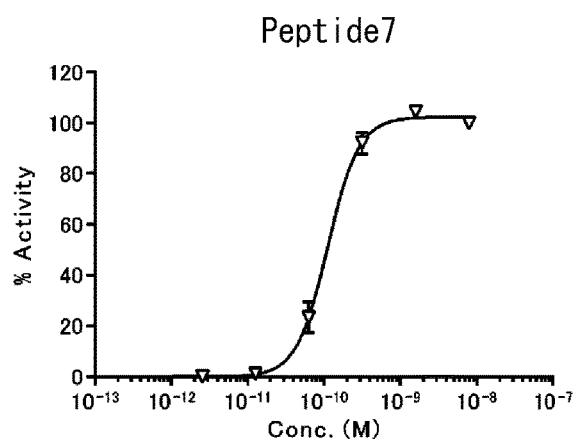
Figure 2:
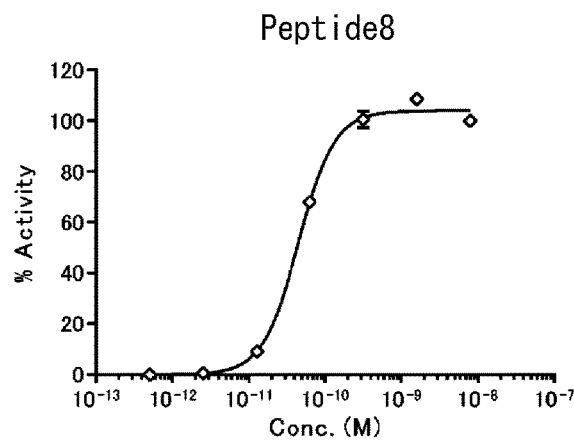
Figure 2:
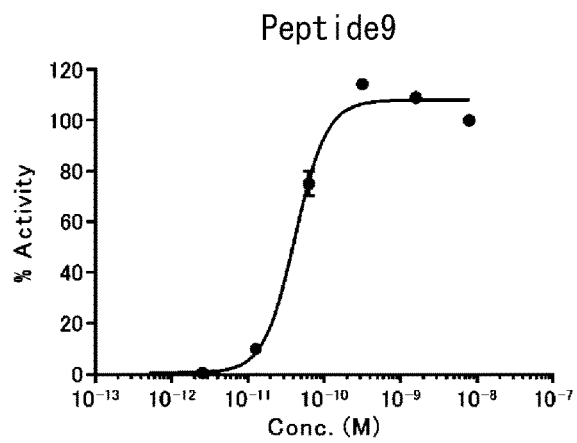

The cAMP assay was carried out using a Hit Hunter cAMP assay for Biologics kit (product of DiscoveRx, Cat. No. 90-0075LM25), according to the included kit instructions. Diluted solutions of peptides 1, 2 and 6 to 9 at different concentrations were mixed with cAMP antibody solution to prepare peptide-cAMP antibody liquid mixtures. Next, the culture medium was removed from the CHO-K1 cell culture plate, washing was performed with PBS, and the peptide-cAMP antibody liquid mixtures were added to the cells and incubated for 30 minutes under a 5% $CO_2$ atmosphere at 37° C. A working detection solution was then added and the culture plate was shielded from light with aluminum foil and then incubated at 25° C. for 1 hour. After incubation, Solution A was added and the culture plate was shielded from light with aluminum foil and then incubated at 25° C. for 3 hours. Finally, the chemiluminescence signal was detected using a GloMax detector (Promega) under conditions of luminescence and integration time (1 sec). The obtained value for the Relative Luminescence Unit (RLU) was analyzed with GraphPad Prism Ver 6.05 (product of Graph Pad) and the $EC_{50}$ value was calculated for each peptide. The results for the $EC_{50}$ value for the cAMP inducing effect of each peptide with the PAC1R or VPAC1R high-expressing cell line are shown in FIG. 1, FIG. 2 and Table 11.

TABLE 11

| Peptide No. | $EC_{50}$ (PAC1R) | $EC_{50}$ (VPAC1R) |
|---|---|---|
| Peptide 1 | 0.052 nM | 0.097 nM |
| Peptide 2 | 0.032 nM | 0.062 nM |
| Peptide 6 | 0.079 nM | 0.093 nM |
| Peptide 7 | 0.112 nM | 0.114 nM |
| Peptide 8 | 0.072 nM | 0.046 nM |
| Peptide 9 | 0.063 nM | 0.043 nM |

The synthesized peptides 1, 2 and 6 to 9 exhibited cAMP inducing ability in the PAC1R and VPAC1R high-expressing cells, and their $EC_{50}$ values were approximately the same as the native peptide (peptide 1: PACAP27).

To summarize the results in Table 6 and Table 11, the peptides of the invention (peptides 6 to 9) have extremely improved stability in aqueous solution compared to PACAP, while also maintaining physiological activity equivalent to that of PACAP. In particular, because they have storage life exceeding 2 years at room temperature, they allow liquid formulations to be developed as products such as vials, ampules and eye drops.

Example 8: cAMP Assay 2 of PACAP27 Modified Peptide

Reagent Preparation

Powders of peptides 3 to 5 and 10 to 28 synthesized in Example 2 were dissolved in water to 0.1 mM, and then diluted to 20 µM with Cell assay buffer (Discove.Rx) (containing 0.5 mM IBMX and 0.001% BSA). A 5-fold dilution series was then prepared with the same Cell assay buffer and used in an assay.

The $EC_{50}$ values of peptides 3 to 5 and 10 to 28 were calculated by the same method as Example 7. The results for the $EC_{50}$ value for the cAMP inducing effect of each peptide with the PAC1 or VPAC1 high-expressing cell line are shown in Table 12.

TABLE 12

| Peptide No. | $EC_{50}$ (PAC1R) | $EC_{50}$ (VPAC1R) |
|---|---|---|
| Peptide 3 | 0.060 nM | 0.101 nM |
| Peptide 4 | 0.040 nM | 0.053 nM |
| Peptide 5 | 0.033 nM | 0.064 nM |
| Peptide 10 | 0.076 nM | 0.101 nM |
| Peptide 11 | 0.038 nM | 0.190 nM |
| Peptide 12 | 0.023 nM | 0.087 nM |
| Peptide 13 | 0.132 nM | 0.072 nM |
| Peptide 14 | 0.074 nM | 0.099 nM |
| Peptide 15 | 0.061 nM | 0.149 nM |
| Peptide 16 | 0.330 nM | 0.065 nM |
| Peptide 17 | 0.099 nM | 0.132 nM |
| Peptide 18 | 0.061 nM | 0.033 nM |
| Peptide 19 | 0.094 nM | 0.044 nM |
| Peptide 20 | 0.080 nM | 0.040 nM |
| Peptide 21 | 0.102 nM | 0.268 nM |
| Peptide 22 | 0.130 nM | 0.457 nM |
| Peptide 23 | 0.079 nM | 0.072 nM |
| Peptide 24 | 0.083 nM | 0.088 nM |
| Peptide 25 | 0.088 nM | 0.028 nM |
| Peptide 26 | 0.066 nM | 0.075 nM |

TABLE 12-continued

| Peptide No. | $EC_{50}$ (PAC1R) | $EC_{50}$ (VPAC1R) |
|---|---|---|
| Peptide 27 | 0.060 nM | 0.044 nM |
| Peptide 28 | 0.084 nM | 0.029 nM |

The peptides of the invention (peptides 3 to 5 and 10 to 28) have extremely improved stability in aqueous solution compared to PACAP, while also maintaining physiological activity equivalent to that of PACAP.

Example 8-2: cAMP Assay 2 of PACAP27 Modified Peptide

Reagent Preparation

Powders of peptides 29 to 34 synthesized in Example 2 were each dissolved in water to 0.1 mM, and then diluted to 20 µM with Cell assay buffer (DiscoveRx) (containing 0.5 mM IBMX and 0.001% BSA). A 5-fold dilution series was then prepared with the same Cell assay buffer and used in an assay.

The $EC_{50}$ values of peptides 27 to 34 were calculated by the same method as Example 7. The results for the $EC_{50}$ value for the cAMP inducing effect of each peptide with the PAC1 or VPAC1 high-expressing cell line are shown in Table 12-2.

TABLE 12-2

| Peptide No. | $EC_{50}$ (PAC1R) | $EC_{50}$ (VPAC1R) |
|---|---|---|
| Peptide 29 | 0.025 nM | 0.090 nM |
| Peptide 30 | 0.032 nM | 0.057 nM |
| Peptide 31 | 0.034 nM | 0.035 nM |
| Peptide 32 | 0.148 nM | 0.076 nM |
| Peptide 33 | 0.089 nM | 0.143 nM |
| Peptide 34 | 0.210 nM | 0.089 nM |

The peptides of the invention (peptides 29 to 34) have extremely improved stability in aqueous solution compared to PACAP, while also maintaining physiological activity equivalent to that of PACAP.

Formulation Examples

A medicine containing a peptide of the invention as an active ingredient can be produced by the following formulation. Drugs of the invention will now be described in greater detail by the formulation examples, with the understanding that the invention is not limited only to these formulation examples.

1. Capsules

| | |
|---|---|
| (1) Peptide 5 | 40 mg |
| (2) Lactose | 70 mg |
| (3) Microcrystalline cellulose | 9 mg |
| (4) Magnesium stearate | 1 mg |
| 1 capsule: | 120 mg |

After mixing the total amounts of (1), (2) and (3) and ½ of (4), the mixture is granulated. The remaining amount of (4) is added and the entire mixture is encapsulated in gelatin capsules.

2. Tablets

|  |  |
|---|---|
| (1) Peptide 6 | 40 mg |
| (2) Lactose | 58 mg |
| (3) Corn starch | 18 mg |
| (4) Microcrystalline cellulose | 3.5 mg |
| (5) Magnesium stearate | 0.5 mg |
| 1 tablet | 120 mg |

After mixing the total amounts of (1), (2) and (3), ⅔ of (4) and ½ of (5), the mixture is granulated. The remaining amounts of (4) and (5) are added to the granules, which are then pressure molded into tablets.

3. Vitreous Injection

| Per 1 ml |  |
|---|---|
| (1) Peptide 5 | 40 mg |
| (2) Refined sucrose | 50 mg |
| (3) Sodium chloride | 2.34 mg |
| (4) Polysorbate80 | s.q. |
| (5) Disodium hydrogenphosphate | s.q. |
| (6) Sodium dihydrogenphosphate | s.q. |
| (7) Sterilized purified water | s.q. |

Components (1) to (6) are dissolved in the sterilized purified water (7) to prepare a vitreous injection.

4. Ophthalmic Drug

| In 100 mL |  |
|---|---|
| (1) Peptide 6 | 100 mg |
| (2) Trometamol | 300 mg |
| (3) Sodium chloride | 900 mg |
| (4) Benzalkonium chloride | s.q. |
| (5) Sterilized purified water | s.q. |

Components (1) to (4) are dissolved in the sterilized purified water (5) and the pH is adjusted to prepare eye drops.

The invention claimed is:

1. A peptide consisting of a sequence or modified sequence wherein, in the sequence represented by the following formula:

$$\text{H-}X_1\text{-D-G-I-F-T-D-}X_2\text{-Y-}X_3\text{-R-Y-R-}X_4\text{-}X_5\text{-}X_6\text{-A-}X_7\text{-}X_8\text{-}X_9\text{-Y-L-A-A-V-}X_{10} \quad (\text{SEQ ID NO: 3})$$

wherein:
$X_1$, $X_2$ and $X_3$ are alanine or serine,
$X_4$, $X_8$ and $X_9$ are lysine or arginine,
$X_5$ is glutamine, alanine or an amino acid having the amide of glutamine replaced with tetrazole,
$X_6$ is methionine, norleucine, alanine or leucine,
$X_7$ is valine or alanine, and
$X_{10}$ is leucine or alanine,
wherein the carboxy group of the aspartic acid residue at position 3 and/or position 8 is replaced with tetrazole, and optionally one, two or three amino acids is deleted from C-terminus of the sequence of SEQ ID NO: 3, or any one sequence selected from the group consisting of:

| | |
|---|---|
| GKRYKQRVKNK; | (SEQ ID NO: 37) |
| GKRYKQRVKN; | (SEQ ID NO: 38) |
| GKRYKQRVK; | (SEQ ID NO: 39) |
| GKRYKQRV; | (SEQ ID NO: 40) |
| GKRYKQR; | (SEQ ID NO: 41) |
| GKRYKQ; | (SEQ ID NO: 42) |
| GKRYK; | (SEQ ID NO: 43) |
| GKRY | (SEQ ID NO: 44) |
| GKR; | |
| GRR; | |
| GK; and | |
| GR | |
| G; | | is added at C-terminus of the sequence of SEQ ID NO: 3.

2. The peptide according to claim 1, wherein the carboxy groups of the aspartic acids at position 3 and position 8 of SEQ ID NO: 3 are replaced with tetrazole.

3. The peptide according to claim 1, wherein the N-terminus of the peptide is acetylated or mesylated.

4. The peptide according to claim 1, wherein the N-terminus of the peptide is acetylated.

5. The peptide according to claim 1, wherein one or two amino acids are deleted from the C-terminus of the sequence of SEQ ID NO:3.

6. A pharmaceutical composition comprising the peptide according to claim 1.

* * * * *

SEQUENCE LISTING

```
<160> NUMBER OF SEQ ID NOS: 44

<210> SEQ ID NO 1
<211> LENGTH: 38
<212> TYPE: PRT
<213> ORGANISM: Homo sapiens

<400> SEQUENCE: 1

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 2
<211> LENGTH: 27
<212> TYPE: PRT
<213> ORGANISM: Homo sapiens

<400> SEQUENCE: 2

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 3
<211> LENGTH: 27
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa is neutral amino acid
<220> FEATURE:
<221> NAME/KEY: MISC_FEATURE
<222> LOCATION: (9)..(9)
```

```
<223> OTHER INFORMATION: Xaa is neutral amino acid
<220> FEATURE:
<221> NAME/KEY: MISC_FEATURE
<222> LOCATION: (11)..(11)
<223> OTHER INFORMATION: Xaa is neutral amino acid
<220> FEATURE:
<221> NAME/KEY: MISC_FEATURE
<222> LOCATION: (15)..(15)
<223> OTHER INFORMATION: Xaa is basic amino acid
<220> FEATURE:
<221> NAME/KEY: MISC_FEATURE
<222> LOCATION: (16)..(16)
<223> OTHER INFORMATION: Xaa is neutral amino acid or amino acid wherein
      amide of glutamine is substituted with tetrazole
<220> FEATURE:
<221> NAME/KEY: MISC_FEATURE
<222> LOCATION: (17)..(17)
<223> OTHER INFORMATION: Xaa is non-polar amino acid
<220> FEATURE:
<221> NAME/KEY: MISC_FEATURE
<222> LOCATION: (19)..(19)
<223> OTHER INFORMATION: Xaa is non-polar amino acid
<220> FEATURE:
<221> NAME/KEY: MISC_FEATURE
<222> LOCATION: (20)..(20)
<223> OTHER INFORMATION: Xaa is basic amino acid
<220> FEATURE:
<221> NAME/KEY: MISC_FEATURE
<222> LOCATION: (21)..(21)
<223> OTHER INFORMATION: Xaa is basic amino acid
<220> FEATURE:
<221> NAME/KEY: MISC_FEATURE
<222> LOCATION: (27)..(27)
<223> OTHER INFORMATION: Xaa is non-polar amino acid

<400> SEQUENCE: 3

His Xaa Asp Gly Ile Phe Thr Asp Xaa Tyr Xaa Arg Tyr Arg Xaa Xaa
1               5                   10                  15

Xaa Ala Xaa Xaa Xaa Tyr Leu Ala Ala Val Xaa
            20                  25

<210> SEQ ID NO 4
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION

<400> SEQUENCE: 4

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 5
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MISC_FEATURE
<222> LOCATION: (3)..(3)
<223> OTHER INFORMATION: Xaa is amino acid wherein carboxy group of
      aspartic acid is substituted with tetrazole

<400> SEQUENCE: 5

His Ser Xaa Gly Ile Phe Thr Asp Ser Tyr Ser Arg Tyr Arg Lys Gln
```

```
1               5                   10                  15
Met Ala Val Lys Lys Tyr Leu Ala Ala Val Leu
            20                  25

<210> SEQ ID NO 6
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 6

His Ser Asp Gly Ile Phe Thr Xaa Ser Tyr Ser Arg Tyr Arg Lys Gln
1               5                   10                  15
Met Ala Val Lys Lys Tyr Leu Ala Ala Val Leu
            20                  25

<210> SEQ ID NO 7
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 7

His Ser Xaa Gly Ile Phe Thr Xaa Ser Tyr Ser Arg Tyr Arg Lys Gln
1               5                   10                  15
Met Ala Val Lys Lys Tyr Leu Ala Ala Val Leu
            20                  25

<210> SEQ ID NO 8
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (17)..(17)
<223> OTHER INFORMATION: Xaa is Nle

<400> SEQUENCE: 8

His Ser Xaa Gly Ile Phe Thr Xaa Ser Tyr Ser Arg Tyr Arg Lys Gln
1               5                   10                  15
```

```
Xaa Ala Val Lys Lys Tyr Leu Ala Ala Val Leu
            20                  25

<210> SEQ ID NO 9
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 9

His Ser Xaa Gly Ile Phe Thr Xaa Ser Tyr Ser Arg Tyr Arg Lys Gln
1               5                   10                  15

Leu Ala Val Lys Lys Tyr Leu Ala Ala Val Leu
            20                  25

<210> SEQ ID NO 10
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (17)..(17)
<223> OTHER INFORMATION: Xaa is Nle

<400> SEQUENCE: 10

His Ser Xaa Gly Ile Phe Thr Xaa Ser Tyr Ser Arg Tyr Arg Lys Gln
1               5                   10                  15

Xaa Ala Val Lys Lys Tyr Leu Ala Ala Val Leu
            20                  25

<210> SEQ ID NO 11
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
```

```
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 11

His Ser Xaa Gly Ile Phe Thr Xaa Ser Tyr Ser Arg Tyr Arg Lys Gln
1               5                   10                  15

Leu Ala Val Lys Lys Tyr Leu Ala Ala Val Leu
            20                  25

<210> SEQ ID NO 12
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 12

His Ser Xaa Gly Ile Phe Thr Xaa Ser Tyr Ser Arg Tyr Arg Lys Gln
1               5                   10                  15

Met Ala Val Lys Lys Tyr Leu Ala Ala Val Leu
            20                  25

<210> SEQ ID NO 13
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: Mesylation
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (17)..(17)
<223> OTHER INFORMATION: Xaa is Nle

<400> SEQUENCE: 13

His Ser Xaa Gly Ile Phe Thr Xaa Ser Tyr Ser Arg Tyr Arg Lys Gln
1               5                   10                  15

Xaa Ala Val Lys Lys Tyr Leu Ala Ala Val Leu
            20                  25
```

```
<210> SEQ ID NO 14
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: Mesylation
<220> FEATURE:
<221> NAME/KEY: misc_feature
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: misc_feature
<222> LOCATION: (8)..(8)
<223> OTHER INFORMATION: Xaa is amino acid wherein carboxy group of
      asparatic acid is substituted with tetrazole

<400> SEQUENCE: 14

His Ser Xaa Gly Ile Phe Thr Xaa Ser Tyr Ser Arg Tyr Arg Lys Gln
1               5                   10                  15

Leu Ala Val Lys Lys Tyr Leu Ala Ala Val Leu
            20                  25

<210> SEQ ID NO 15
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (16)..(16)
<223> OTHER INFORMATION: Xaa is amino acid wherein amide group of
      glutamine is substituted with tetrazole

<400> SEQUENCE: 15

His Ser Xaa Gly Ile Phe Thr Xaa Ser Tyr Ser Arg Tyr Arg Lys Xaa
1               5                   10                  15

Leu Ala Val Lys Lys Tyr Leu Ala Ala Val Leu
            20                  25

<210> SEQ ID NO 16
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
``` asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 16

His Ala Xaa Gly Ile Phe Thr Xaa Ser Tyr Ser Arg Tyr Arg Lys Gln
1               5                   10                  15

Leu Ala Val Lys Lys Tyr Leu Ala Ala Val Leu
            20                  25

<210> SEQ ID NO 17
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 17

His Ser Xaa Gly Ile Phe Thr Xaa Ala Tyr Ser Arg Tyr Arg Lys Gln
1               5                   10                  15

Leu Ala Val Lys Lys Tyr Leu Ala Ala Val Leu
            20                  25

<210> SEQ ID NO 18
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 18

His Ser Xaa Gly Ile Phe Thr Xaa Ser Tyr Ala Arg Tyr Arg Lys Gln
1               5                   10                  15

Leu Ala Val Lys Lys Tyr Leu Ala Ala Val Leu
            20                  25

<210> SEQ ID NO 19
<211> LENGTH: 27
<212> TYPE: PRT

```
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
     asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
     asparatic acid is substituted with tetrazole

<400> SEQUENCE: 19

His Ser Xaa Gly Ile Phe Thr Xaa Ser Tyr Ser Arg Tyr Arg Lys Ala
1               5                   10                  15

Leu Ala Val Lys Lys Tyr Leu Ala Ala Val Leu
            20                  25

<210> SEQ ID NO 20
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
     asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
     asparatic acid is substituted with tetrazole

<400> SEQUENCE: 20

His Ser Xaa Gly Ile Phe Thr Xaa Ser Tyr Ser Arg Tyr Arg Lys Gln
1               5                   10                  15

Ala Ala Val Lys Lys Tyr Leu Ala Ala Val Leu
            20                  25

<210> SEQ ID NO 21
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
     asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
     asparatic acid is substituted with tetrazole

<400> SEQUENCE: 21
```

```
His Ser Xaa Gly Ile Phe Thr Xaa Ser Tyr Ser Arg Tyr Arg Lys Gln
1               5                   10                  15

Leu Ala Ala Lys Lys Tyr Leu Ala Ala Val Leu
            20                  25

<210> SEQ ID NO 22
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 22

His Ser Xaa Gly Ile Phe Thr Xaa Ser Tyr Ser Arg Tyr Arg Lys Gln
1               5                   10                  15

Leu Ala Val Lys Lys Tyr Leu Ala Ala Val Ala
            20                  25

<210> SEQ ID NO 23
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 23

His Ser Xaa Gly Ile Phe Thr Xaa Ser Tyr Ser Arg Tyr Arg Arg Gln
1               5                   10                  15

Leu Ala Val Arg Arg Tyr Leu Ala Ala Val Leu
            20                  25

<210> SEQ ID NO 24
<211> LENGTH: 30
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 24

His Ser Xaa Gly Ile Phe Thr Xaa Ser Tyr Ser Arg Tyr Arg Arg Gln
1               5                   10                  15

Leu Ala Val Arg Arg Tyr Leu Ala Ala Val Leu Gly Arg Arg
            20                  25                  30

<210> SEQ ID NO 25
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 25

His Ser Xaa Ala Ile Phe Thr Xaa Ser Tyr Ser Arg Tyr Arg Lys Gln
1               5                   10                  15

Leu Ala Val Lys Lys Tyr Leu Ala Ala Val Leu
            20                  25

<210> SEQ ID NO 26
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 26

His Ala Xaa Gly Ile Phe Thr Xaa Ala Tyr Ser Arg Tyr Arg Lys Gln
1               5                   10                  15

Leu Ala Val Lys Lys Tyr Leu Ala Ala Val Leu
            20                  25
```

```
<210> SEQ ID NO 27
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 27

His Ala Xaa Gly Ile Phe Thr Xaa Ser Tyr Ser Arg Tyr Arg Lys Gln
1               5                   10                  15

Ala Ala Val Lys Lys Tyr Leu Ala Ala Val Leu
            20                  25

<210> SEQ ID NO 28
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 28

His Ser Xaa Gly Ile Phe Thr Xaa Ala Tyr Ser Arg Tyr Arg Lys Ala
1               5                   10                  15

Leu Ala Val Lys Lys Tyr Leu Ala Ala Val Leu
            20                  25

<210> SEQ ID NO 29
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
``` asparatic acid is substituted with tetrazole

<400> SEQUENCE: 29

His Ser Xaa Gly Ile Phe Thr Xaa Ala Tyr Ser Arg Tyr Arg Lys Gln
1               5                   10                  15

Ala Ala Val Lys Lys Tyr Leu Ala Ala Val Leu
            20                  25

<210> SEQ ID NO 30
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 30

His Ser Xaa Gly Ile Phe Thr Xaa Ser Tyr Ser Arg Tyr Arg Lys Ala
1               5                   10                  15

Ala Ala Val Lys Lys Tyr Leu Ala Ala Val Leu
            20                  25

<210> SEQ ID NO 31
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: Mesylation
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 31

His Ser Xaa Gly Ile Phe Thr Xaa Ala Tyr Ser Arg Tyr Arg Lys Gln
1               5                   10                  15

Leu Ala Val Lys Lys Tyr Leu Ala Ala Val Leu
            20                  25

<210> SEQ ID NO 32
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES

```
<222> LOCATION: (1)..(1)
<223> OTHER INFORMATION: Mesylation
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 32

His Ser Xaa Ala Ile Phe Thr Xaa Ser Tyr Ser Arg Tyr Arg Lys Gln
1               5                   10                  15

Leu Ala Val Lys Lys Tyr Leu Ala Ala Val Leu
            20                  25

<210> SEQ ID NO 33
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD
<222> LOCATION: (1)..(1)
<223> OTHER INFORMATION: Mesylation
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 33

His Ser Xaa Ala Ile Phe Thr Xaa Ser Tyr Ser Arg Tyr Arg Lys Gln
1               5                   10                  15

Ala Ala Val Lys Lys Tyr Leu Ala Ala Val Leu
            20                  25

<210> SEQ ID NO 34
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 34

His Ser Xaa Ala Ile Phe Thr Xaa Ser Tyr Ser Arg Tyr Arg Lys Gln
1               5                   10                  15

Ala Ala Val Lys Lys Tyr Leu Ala Ala Val Leu
```

```
<210> SEQ ID NO 35
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 35

His Ala Xaa Ala Ile Phe Thr Xaa Ser Tyr Ser Arg Tyr Arg Lys Gln
1               5                   10                  15

Ala Ala Val Lys Lys Tyr Leu Ala Ala Val Leu
            20                  25

<210> SEQ ID NO 36
<211> LENGTH: 27
<212> TYPE: PRT
<213> ORGANISM: Artificial Sequence
<220> FEATURE:
<223> OTHER INFORMATION: Syntehtic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is amino acid wherein carboxy group of
      asparatic acid is substituted with tetrazole
<220> FEATURE:
<221> NAME/KEY: MISC_FEATURE
<222> LOCATION: (8)..(8)
<223> OTHER INFORMATION: Xaa is amino acid wherein carboxy group of
      asparatic acid is substituted with tetrazole

<400> SEQUENCE: 36

His Ser Xaa Ala Ile Phe Thr Xaa Ser Tyr Ser Arg Tyr Arg Lys Ala
1               5                   10                  15

Ala Ala Val Lys Lys Tyr Leu Ala Ala Val Leu
            20                  25

<210> SEQ ID NO 37
<211> LENGTH: 11
<212> TYPE: PRT
<213> ORGANISM: Artificial Sequence
<220> FEATURE:
<223> OTHER INFORMATION: Synthetic peptide

<400> SEQUENCE: 37

Gly Lys Arg Tyr Lys Gln Arg Val Lys Asn Lys
1               5                   10

<210> SEQ ID NO 38
<211> LENGTH: 10
<212> TYPE: PRT
```

```
<213> ORGANISM: Artificial Sequence
<220> FEATURE:
<223> OTHER INFORMATION: Synthetic peptide

<400> SEQUENCE: 38

Gly Lys Arg Tyr Lys Gln Arg Val Lys Asn
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Gly Lys Arg Tyr Lys Gln Arg Val Lys
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic peptide

<400> SEQUENCE: 40

Gly Lys Arg Tyr Lys Gln Arg Val
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic peptide

<400> SEQUENCE: 41

Gly Lys Arg Tyr Lys Gln Arg
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic peptide

<400> SEQUENCE: 42

Gly Lys Arg Tyr Lys Gln
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic peptide

<400> SEQUENCE: 43

Gly Lys Arg Tyr Lys
1               5

<210> SEQ ID NO 44
<211> LENGTH: 4
<212> TYPE: PRT
<213> ORGANISM: Artificial Sequence
```

```
<220> FEATURE:
<223> OTHER INFORMATION: Synthetic peptide

<400> SEQUENCE: 44

Gly Lys Arg Tyr
1
```